US006707548B2

(12) United States Patent
Kreimer et al.

(10) Patent No.: US 6,707,548 B2
(45) Date of Patent: Mar. 16, 2004

(54) SYSTEMS AND METHODS FOR FILTER BASED SPECTROGRAPHIC ANALYSIS

(75) Inventors: David I. Kreimer, Berkeley, CA (US); Oleg A. Yevin, Walnut Creek, CA (US); Robert Weber, Menlo Park, CA (US)

(73) Assignee: Array Bioscience Corporation, Oakland, CA (US)

( * ) Notice: Subject to any disclaimer, the term of this patent is extended or adjusted under 35 U.S.C. 154(b) by 0 days.

(21) Appl. No.: 09/939,887

(22) Filed: Aug. 27, 2001

(65) Prior Publication Data

US 2003/0227628 A1 Dec. 11, 2003

Related U.S. Application Data

(60) Provisional application No. 60/267,329, filed on Feb. 8, 2001.

(51) Int. Cl.[7] .............................. G01J 3/44; G01N 21/65

(52) U.S. Cl. .................... 356/301; 356/302; 356/320

(58) Field of Search ........................... 356/301, 302, 356/303, 317, 318, 320, 414, 416, 419; 250/227.23, 338.5

(56) References Cited

U.S. PATENT DOCUMENTS

| | | | |
|---|---|---|---|
| 4,483,929 A | | 11/1984 | Szoka |
| 4,692,875 A | * | 9/1987 | Riley et al. ............ 364/497 |
| 4,964,457 A | | 10/1990 | Leonard et al. |
| 5,112,127 A | | 5/1992 | Carrabba et al. |
| 5,194,913 A | | 3/1993 | Myrick et al. |
| 5,255,067 A | | 10/1993 | Carrabba et al. |
| 5,266,498 A | | 11/1993 | Tarcha et al. |
| 5,306,403 A | | 4/1994 | Vo-Dinh |
| 5,334,296 A | | 8/1994 | Henkins et al. |

(List continued on next page.)

FOREIGN PATENT DOCUMENTS

| | | |
|---|---|---|
| EP | 0 587 008 | 2/1999 |
| JP | 59-15792 A | 1/1984 |
| SU | 1064-115 A | 12/1983 |

(List continued on next page.)

OTHER PUBLICATIONS

Copy of International Search Report mailed Jul. 16, 2002.

Andres, R.P., "Self–Assembly of a Two–Dimensional Superlattice of Molecularly Linked Metal Clusters," *Science*, vol. 273, Sep. 20, 1996, pp. 1690–1693.

(List continued on next page.)

Primary Examiner—Frank G. Font
Assistant Examiner—Layla Lauchman
(74) Attorney, Agent, or Firm—Fliesler Dubb Meyer & Lovejoy LLP

(57) ABSTRACT

Systems and methods for filter based spectrographic analysis are provided that permit rapid analysis of bioanalytes. Systems include devices for illuminating a sample with electromagnetic radiation and capturing radiation emitted from the sample. Emitted radiation can be collected by a plurality of waveguides each associated with a filter for a particular wavelength of radiation. Focusing devices are associated with filters and waveguides in certain embodiments. Radiation captured by waveguides can then be transmitted to a remote detector, which can determine the intensity of radiation for each waveguide. The use of a plurality of filters having different, band pass characteristics can permits the simultaneous detection of a plurality of different wavelengths of radiation emitted by a sample, thereby providing spectrographic information about the sample under study. Systems can include computers for storing acquired spectrographic information, addressable arrays of samples, and information security measures. Spectrographic information of samples can be diagnostic tools for identifying and quantifying a variety of different materials, including bioanalytes.

61 Claims, 19 Drawing Sheets

U.S. PATENT DOCUMENTS

| | | |
|---|---|---|
| 5,376,556 A | 12/1994 | Tarcha et al. |
| 5,391,272 A | 2/1995 | O'Daly et al. |
| 5,400,136 A | 3/1995 | Vo-Dinh |
| 5,404,218 A | 4/1995 | Nave et al. |
| 5,445,972 A | 8/1995 | Tarcha et al. |
| 5,468,644 A | 11/1995 | Stephenson et al. |
| 5,498,875 A | 3/1996 | Obremski et al. |
| 5,506,678 A | 4/1996 | Carlsen et al. |
| 5,538,613 A | 7/1996 | Brumley et al. ............ 204/612 |
| 5,567,628 A | 10/1996 | Tarcha et al. |
| 5,591,975 A | 1/1997 | Jack et al. ............... 250/338.5 |
| 5,604,587 A | 2/1997 | Che et al. |
| 5,615,673 A | 4/1997 | Berger et al. |
| 5,621,522 A | 4/1997 | Ewing et al. |
| 5,630,924 A | 5/1997 | Fuchs et al. |
| 5,632,957 A | 5/1997 | Heller et al. |
| 5,693,152 A | 12/1997 | Carron |
| 5,707,587 A * | 1/1998 | Blanchard et al. ............ 422/82 |
| 5,720,339 A | 2/1998 | Glass |
| 5,721,102 A | 2/1998 | Vo-Dinh |
| 5,783,389 A | 7/1998 | Vo-Dinh |
| 5,814,516 A | 9/1998 | Vo-Dinh |
| 5,814,565 A | 9/1998 | Reichert et al. |
| 5,836,317 A | 11/1998 | Kunst |
| 5,839,290 A | 11/1998 | Nazeri |
| 5,842,995 A | 12/1998 | Mahadebvan-Jansen et al. ......................... 600/473 |
| 5,864,397 A | 1/1999 | Vo-Dinh |
| 5,866,430 A | 2/1999 | Grow |
| 5,891,738 A | 4/1999 | Soini et al. |
| 5,938,617 A | 8/1999 | Vo-Dinh |
| 5,982,484 A | 11/1999 | Clarke et al. ............... 356/301 |
| 6,025,202 A | 2/2000 | Natan |
| 6,033,546 A | 3/2000 | Ramsey |
| 6,040,906 A | 3/2000 | Harhay |
| 6,044,285 A | 3/2000 | Chaiken et al. |
| 6,064,897 A * | 5/2000 | Lindberg et al. ............ 600/316 |
| 6,071,394 A | 6/2000 | Cheng et al. |
| 6,087,182 A | 7/2000 | Jeng et al. |
| 6,099,803 A | 8/2000 | Ackley et al. |
| 6,126,901 A | 10/2000 | Patch et al. |
| 6,141,095 A | 10/2000 | Allen et al. |
| 6,149,868 A | 11/2000 | Natan et al. |
| 6,181,957 B1 | 1/2001 | Lambert et al. |
| 6,274,385 B1 | 8/2001 | Hochlowski et al. |
| 6,281,971 B1 | 8/2001 | Allen et al. .................. 356/301 |
| 2002/0015150 A1 | 2/2002 | Armstrong et al. |

FOREIGN PATENT DOCUMENTS

| | | |
|---|---|---|
| WO | WO 95/33189 | 12/1995 |
| WO | WO 98/50777 | 11/1998 |
| WO | WO 99/44065 | 2/1999 |
| WO | WO 99/44045 | 9/1999 |
| WO | WO 99/67623 | 12/1999 |
| WO | WO 99/67641 | 12/1999 |
| WO | WO 01/06257 | 1/2001 |
| WO | WO 01/15288 | 3/2001 |
| WO | WO 01/25758 A1 | 4/2001 |
| WO | WO 01/33189 A2 | 5/2001 |

OTHER PUBLICATIONS

Campion, A. and Kambhampati, P., Surface–Enhanced Raman Scattering, *Chemical Society Reviews*, 1998, vol. 27, pp. 241–250.

Chee, M., et al., "Accessing Genetic Information with High–Density DNA Arrays," *Science*, vol. 274, Oct. 25, 1996, pp. 610–614.

Danilova, Y.E., et al., "Absorption Spectra and Photomodification of Silver Fractal Clusters," *Fractal Reviews in the Natural and Applied Sciences*, Institute of Automation and Electrometry, Russian Academy of Science, Siberian Branch, pp. 101–112.

Elghanian, R., et al., "Selective Colorimetric Detection of Polynucleotides Based on the Distance–Dependent Optical Properties of Gold Nanoparticles," *Science*, vol. 277, Aug. 22, 1997, pp. 1078–1081.

Gadenne, P., et al., "Giant Stokes Fields on Semicontinuous Metal Films," *J. Opt. Soc. Am. B*/vol. 15, No. 1, Jan. 1998, pp. 68–72.

Graham, D., et al., "Selective Detection of Deoxyribonucleic Acid at Ultralow Concentrations by SERRS," *Analytical Chemistry*, vol. 69, No. 22, Nov. 15, 1997, pp. 4703–4707.

Hacia, J.G., et al., "Enhanced high density oligonucleotide array–based sequence analysis using modified nucleoside triphosphates," *Nucleic Acids Research*, 1998, vol. 26, No. 21, pp. 4975–4982.

Igloi, G.L., "Variability in the Stability of DNA–Peptide Nucleic Acid (PNA) Single–Base Mismatched Duplexes-:Real–Time Hybridization During Affinity Electrophoresis in PNA–Containing Gels," *Proc. Natl. Acad. Sci. USA*, vol. 95, Jul. 1998 Biochemistry, pp. 8562–8567.

Ingram, R.S., et al., Poly–hetero–functionalized Alkanethiolate–Stabilized Gold Cluster Compounds, *J. Am. Chem. Soc.*, 1997, vol. 119, pp. 9175–9178.

Jones, J.C., et al., "Quantitative Assessment of Surface–Enhanced Resonance Raman Scattering For the Analysis of Dyes on Colloidal Silver," *Analytical Chemistry*, vol. 71, No. 3, Feb. 1, 1999, pp. 596–601.

Kim, W., et al., "Fractals in Microcavities: Giant Coupled, Multiplicative Enhancement of Optical Responses," *Physicals Review Letters*, vol. 82, No. 24, Jun. 14, 1999, pp. 4811–4814.

Kneipp, K., et al., "Detection and Identification of a Single DNA Base Molecule Using Surface–Enhanced Raman Scattering (SERS)," *Physical Review E*, vol. 57, No. 6, Jun. 1998, pp. R6281–R6284.

Kneipp, K., et al., "Single Molecule Detection Using Surface–Enhanced Raman Scattering (SERS)," *Physical Review Letters*, vol. 78, No. 9, Mar. 3, 1997, pp. 1667–1670.

Kurokawa, Y., et al., "Surface–Enhanced Raman Spectroscopic Detection $CO^{2-}{}_3$, $SO^{2-}{}_3$, and Nucleic Acid Bases Using Polyvinyl Alcohol Film Doped with Ag Fine Particles," *Analytical Biochemistry* 209, 1993, pp. 247–250.

Lisy, V., et al., "Internal DNA Modes Below 25 $cm^{-1}$: A Resonance Raman Spectroscopy Observation," *Journal of Biomolecular Structure & Dynamics*, ISSN 0739–1102, vol. 14, Issue No. 4, 1997, pp. 517–523.

Michael, K.L., et al., "Randomly Ordered Addressable High–Density Optical Sensor Arrays," *Analytical Chemistry*, vol. 70, No. 7, Apr. 1, 1998, pp. 1242–1248.

Mucic, R.C., et al., "DNA–Directed Synthesis of Binary Nanoparticle Network Materials," *J. Am. Chem. Soc.*, 1998; vol. 120, pp. 12674–12675.

Nie, S. et al., "Probing Single Molecules and Single Nanoparticles by Surface–Enhanced Raman Scattering," *Science*, vol. 275, Feb. 21, 1997, pp. 1102–1106.

Owen, J.F., et al., "Enhancement of Fluorescence Induced by Microstructure Resonances of a Dielectric Fiber," *Physical Review Letters*, vol. 47, No. 15, Oct. 12, 1981, pp 1075–1078.

Peterlinz, K.A., et al., "Observation of Hybridazation and Dehybridization of Thiol–Tethered DNA Using Two–Color Surface Plasmon Resonance Spectroscopy," *J. Am. Chem. Soc.*, vol. 119, No. 14, 1997, pp. 3401–3402.

Plekhanov, A.I., et al., "Production and Spectroscopic Study of Silver Fractal Clusters by Laser Vaporization of Target," *Opt. Spectrosc. (USSR)* 71 (5), Nov. 1991, pp. 451–454.

Ratilainaen, T., et al., "Hybridization of Peptide Nucleic Acid," *Biochemistry 1998*, 37, pp. 12331–12342.

Safonov, V.P., et al., "Spectral Dependence of Selective Photomodification in Fractal Aggregates of Colloidal Particles," *Physical Review Letters*, vol. 80, No. 5, Feb. 2, 1998, pp. 1102–1105.

Weitz, D.A., et al., "Colloidal Aggregation Revisited: New Insights Based on Fractal Structure and Surface–Enhanced Raman Scattering," *Surface Science,*k vol. 158, 1985, pp. 147–164.

Xiao, T., et al., "Hunting for the Active Sites of Surface–Enhanced Raman Scattering: A New Strategy Based on Single Silver Particles," *Physical Review Letters*, vol. 78, No. 9, Mar. 3, 1997, pp. 632–638.

Shalaev, V.M., "Nonlinear Optics of Random Media: Fractal Composites and Metal–Dielectric Films," *Springer Tracts in Modern Physics*, pp. 101–147.

Zou, S., et al., "Surface–Enhanced Raman Scattering of Ultrathin Cadmium Chalcogenide Films on Gold Formed by Electrochemical Atomic–Layer Epitaxy: Thickness–Dependent Phonon Characteristics," *J. Phys. Chem. B 1999*, 103, pp. 2323–2326.

"FieldSpec®Pro—User's Guide," pp. 1–83, Feb. 2000.

McClain, et al., "Fast Chemical Imaging—A Rapid, Noninvasive Tool for Medical, Materials, and Process Analyses,", *Spectroscopy*, Sep. 2000, pp. 28–37.

Paul, et al., "Enabling New Imaging Applications for Fiber Optic Bundles," *Collimated Holes, Inc.*, Apr. 1995, pp. 1–4.

Stikeman, "Innovation: The ForeFront of Emerging Technology, R & D and Market Trends—Biochips Go Birg Time," *Technology Review*, Mar. 2001.

"Background Filtering in Fiber Optic Raman Sampling Probes," *InPhotonics, Inc.*, 1999, pp. 1–2.

Chrien, et al., "Imaging Spectrometry Using Liquid Crystal Tunable Filters," Apr. 1993, pp. 1–11.

* cited by examiner

SYSTEMS AND METHODS FOR FILTER BASED SPECTROGRAPHIC ANALYSIS

RELATED APPLICATION

This utility application claims priority to U.S. Provisional Patent Application Ser. No: 60/267,329, filed Feb. 8, 2001.

BACKGROUND OF THE INVENTION

1. Field of the Invention

This invention relates to spectroscopy, in particular, devices and methods for spectrographic analyses that use filters to select wavelengths of electromagnetic radiation for measurement.

2. Description of Related Art

Spectroscopy can be characterized as the study of relationships between absorption and/or emission of electromagnetic radiation by certain substances as a function of the wavelength of the radiation. Absorption spectroscopy is in widespread use for the detection and identification of substances because a substance absorbs electromagnetic radiation better at certain wavelengths than at others. When a substance is exposed to a poorly absorbed wavelength of electromagnetic radiation, much of that radiation is reflected or transmitted back into the surrounding medium. A photodetector nearby can detect the radiation, and the amount of radiation can be quantified. In contrast, when a substance is exposed to an efficiently absorbed wavelength, little of that radiation is reflected into the surrounding medium, and consequently, the amount of radiation detected is less than for a poorly absorbed wavelength. Measurements are typically made over a range of wavelengths, and can include very short wavelengths (e.g., gamma- rays or x-rays) to very long wavelengths (e.g., radio frequency radiation). The relationship between radiation intensity and wavelength is herein termed a "spectrum." As used here, the term "spectrum" includes, but is not limited to absorption, fluorescence, Raman, emission, or any other form or type of electromagnetic radiation. For many analytical applications, wavelengths in ultraviolet, visible and/or infrared ranges are especially useful.

Individual substances either absorb or emit characteristic wavelengths of electromagnetic radiation. Each substance thus has a characteristic spectrum, which can be used to identify and/or quantify the amount of a particular substance. Many volumes in the spectroscopic literature are devoted to the presentation of data regarding spectra of individual substances.

However, existing methods and apparatus have several drawbacks. Most spectroscopic apparatus rely upon varying the wavelength of emitted radiation from a radiation source by means of a dispersion device such as a prism or a diffraction grating. A dispersion device decomposes electromagnetic radiation of heterogeneous wavelengths into spatially resolved beams of fairly monochromatic radiation. The dispersion is achieved as follows: An electromagnetic radiation is collimated in a beam to allow the beam to fall onto a prism or grating under appropriate angle of incidence. Radiation of various wavelengths present in the beam interferes with such a dispersion device in a wavelength-dependent manner. This produces a plurality of fairly monochromatic beams radiated under various, wavelength-dependent angles. Each beam is collected onto the surface of a photosensitive device (such as a photo-multiplying tube, also called PMT, or photo-diode, or photo-sensitive film). The intensity of monochromatic light in such a beam is analyzed as the function of spatial position of the beam. The position is directly related to the wavelength in the beam. This way of spectra acquisition is broadly employed in various spectrophotometers and spectrographs. A major drawback of this approach is a high cost for such instrumentation, which is to a large extend due to a need for precise alignment of optical elements.

A source of electromagnetic radiation (e.g., a light source) produces a beam of radiation that enters a dispersion device. By way of example, a prism separates the different wavelengths at different angles depending on the index of refraction of each wavelength as it is transmitted through the prism. In the case of visible light, the result can be a "rainbow." To expose an analyte sample to a particular wavelength, the prism is adjusted so that the angle of refraction of the radiation directs a relatively narrow range of wavelengths to the sample for spectroscopic measurement. To obtain a spectrum, the wavelength is varied by rotating the prism to direct other wavelengths to the sample. Similar methods can be applied to diffraction gratings. These processes are relatively slow, in that the rate of change of wavelength of illuminating radiation must be sufficiently slow to permit accurate measurement of absorption at each wavelength.

The length of time required to obtain a spectrum over a desired range of wavelengths depends upon the range desired, the discrimination between wavelengths, and upon the number of samples to be analyzed. For analyses of multiple samples, traditional spectroscopic methods can be impractically long. Moreover, prisms and diffraction gratings must be aligned carefully and misalignment can result in errors that may be difficult to detect.

SUMMARY OF THE INVENTION

To overcome these and other disadvantages of traditional spectroscopic devices and methods, certain embodiments of this invention use a plurality of narrow-band pass filters to select wavelengths of electromagnetic radiation for analysis. Each filter can be associated with an individual detector, for example, a charge coupled device ("CCD"), forming a "filter/detector unit". Radiation emitted by a sample can penetrate through a filter and can be detected and/or quantified and can be displayed on an output device and/or stored in electronic form on a computer. The filter can absorb radiation of other wavelengths, preventing those wavelengths from being detected. Additional filters having desired transmittance at other, selected wavelengths can be used simultaneously to detect absorption at those desired wavelengths.

Multiple filter/detector units can be placed in a one- or two-dimensional arrangement relative to each other, permitting the simultaneous measurement of absorbed radiation at a number of different wavelengths from a single sample of the substance to be analyzed. Outputs from each detector can be displayed along, for example, a vertical axis of a two-dimensional plot, and the band-pass wavelength of the filter can be displayed along a horizontal axis, for example, similar to a conventional spectrogram. Thus, a spectrum can be obtained over a desired range of wavelengths. Addressable arrays of samples can be analyzed in an automated fashion. A series of samples can be applied to a substrate, each sample having a unique identifier, either position on the array, or by way of a unique chemical marker. Systems for spectrographic analysis can include servo-controlled probes that can acquire spectrographic information from each of a plurality of samples so arrayed.

It can be readily appreciated that similar strategies can be employed for emission, fluorescence, Raman, and any other kind of spectra, and other types of plots (e.g., three-dimensional displays) can be readily prepared.

In certain embodiments, filters can be chosen to permit passage of a relatively narrow wavelength band of radiation. Such embodiments can be useful in situations in which a desired spectrographic feature is narrow.

In certain other embodiments, filters can be chosen to permit passage of a relatively wide wavelength band of radiation. Such embodiments can be useful in situations in which desired spectrographic features are broad, or in which the desired information has sufficiently high intensity and is not masked by signals at other wavelengths within the band detected.

In yet other embodiments, a portion of a spectrum can be obtained using filter/detector units having wavelength bands that are sufficiently near each other to provide substantially complete coverage throughout a desired wavelength range. In other embodiments, it can be desirable to select only certain portions of a spectrum for analysis.

In additional embodiments of this invention, filter/detector units can include waveguides, including light pipes to transmit radiation from a sample to a remote detector.

Many configurations of sample, sample substrate, waveguides, focusing lenses and detectors are possible. In certain embodiments, a plurality of samples can be prepared on a substrate in an array, and samples can be "read" sequentially.

Certain embodiments employ lenses or other means to focus radiation emitted by a sample onto a waveguide for transmission to a detector. Focusing can increase the intensity of the signal detected and/or can decrease the amount of radiation arising from other samples in an array ("parasite radiation") which can confound the analysis of certain spectrographic features.

Spectrographic information from small samples or a portion of a sample can be obtained using the above strategy along with microscopes. Resolution of microscopic detection of spectra can depend upon the wavelengths of interest, with features in low wavelength portions of the electromagnetic spectrum (e.g., violet/ultraviolet) permitting finer detail than for features having longer wavelengths (e.g., infrared).

In other embodiments, the filters can be miniaturized and arranged in a one- or a two-dimensional array to permit the simultaneous measurement of absorption at different wavelength bands of a relatively small sample.

In yet other embodiments of this invention, arrays of miniaturized filter/detector units can be formed as a probe and can be positioned sequentially over different samples. Such embodiments can be especially desired for spectrographic analysis of multiple samples on a substrate.

In yet further embodiments, a plurality of arrays of miniaturized filter/detector units can be used simultaneously to obtain spectrographic analyses of a multiplicity of samples simultaneously.

In certain other embodiments, the filters can be of fixed band-pass, or alternatively, in other embodiments, can be made "tunable" using electric field-sensitive liquid crystal materials and/or any other materials possessing the desired, similar optical and/or electrical properties.

The apparatus and methods of this invention can avoid many of the problems facing conventional spectrophotometric methods and apparatus. In situations in which the different filters have fixed wavelength band ranges, the problems of optical alignment can be reduced. Because such filters can be made reproducibly, wavelength drift can be minimized. Moreover, the lack of a requirement for sophisticated moving parts can permit manufacture of relatively inexpensive, yet accurate spectrographic devices.

The use of multiple filter/detector units can permit the simultaneous measurement of a desired spectrum or portion thereof, which can substantially reduce the length of time required for spectrographic analyses. By providing accurate rapid analyses, the devices and methods of this invention can permit study of volatile and/or fragile analytes. By way of example, an analyte that is easily vaporized can be detected sufficiently rapidly to permit acquisition of a broad range of wavelengths simultaneously. In contrast, prior art dispersion based methods can suffer from artifacts in the spectrum due to loss of sample during the analysis. Specifically, later-measured wavelengths can have artificially low signal intensity due to loss of the analyte, and the true relationship between peak intensities can be misrepresented. Similarly, for analytes that are labile, i.e., that are fragile and can degrade easily, the devices and methods of this invention can provide improved spectra. As with volatile analytes, prior art dispersion based methods and devices can result in later-measured wavelengths being under represented relative to earlier-measured wavelengths. Moreover, using the devices and methods of this invention, spectra can be obtained under a variety of different ambient conditions including reduced temperature and/or chemical milieu. Thus, conditions can be selected that can reduce artifacts and result in more accurate, reproducible spectrographic analyses.

Devices and methods of this invention can be used for analyte detection, identification of substances for materials science applications, and astrophysical studies of radiation emitted by remote objects. For example, gamma-radiation and x-radiation can provide important information concerning stars, galaxies quasars, neutron stars and other astrophysical phenomena. Infrared and/or radio frequency detectors can be useful for studying features opaque to visible radiation, including surface features of planets having atmospheres.

BRIEF DESCRIPTION OF THE DRAWINGS

The invention will be described with respect to the particular embodiments thereof. Other objects, features, and advantages of the invention will become apparent with reference to the specification and drawings in which:

FIG. 3a depicts an embodiment having lenses and FIG. 3b depicts an embodiment not having lenses.

FIG. 9a is a top view depicting several sample detection areas arranged in circular array. FIG. 9b is a side view of the reader head.

FIG. 13a depicts an embodiment comprising a bundle of waveguides having circular cross-sections. FIG. 13b depicts a bundle of waveguides having rectangular cross-sections. FIG. 13c depicts a bundle of waveguides having hexagonal cross-sections. FIG. 13d depicts a bundle of waveguides having triangular cross-sections.

FIG. 14a depicts several waveguides with detectors. FIG. 14b depicts a higher density of waveguides and detectors than in FIG. 14a.

DETAILED DESCRIPTION OF THE INVENTION

Electromagnetic radiation coming from a sample or in a beam can provide valuable information on chemical and physical properties of matter in that sample. Acquisition of spectrographic information is a broadly applied means for detecting, identifying and/or characterizing samples or the sources of electromagnetic radiation. Techniques for acquisition and analysis of spectral information is called spectroscopy.

Use of the systems and methods disclosed herein have broad applications in biology, healthcare, agricultural research, pharmacology, drug search, drug discovery, biomedical research including human immunodeficiency virus (HIV), genetic testing, blood screening, genomics, and proteomics. Examples of some of the biomolecules that can be of relevance include DNA, RNA, lipids, nucleotides, proteins, peptides, amino acids, sugars, polysaccharides, hormones, neurotransmitters, vitamins, regulatory factors, metabolic intermediates, antibodies, and combinations of the above. Some embodiments of this invention can be useful for assessing relationships between gene expression, protein synthesis, and biological function of gene expression and protein synthesis. Systems and methods of this invention can also be used to assess the roles, for example, of neurotransmitters, hormones, and enzymes in health and disease.

Systems and methods of this invention can also be used to provide a plurality of analyses in a simple assay procedure. Biochips can be read using the systems of this invention that can provide identification of microbes including viruses, bacterial, bacterial products, toxins and plasmids, fungi, fungal products and fungal toxins.

Figure 1A:
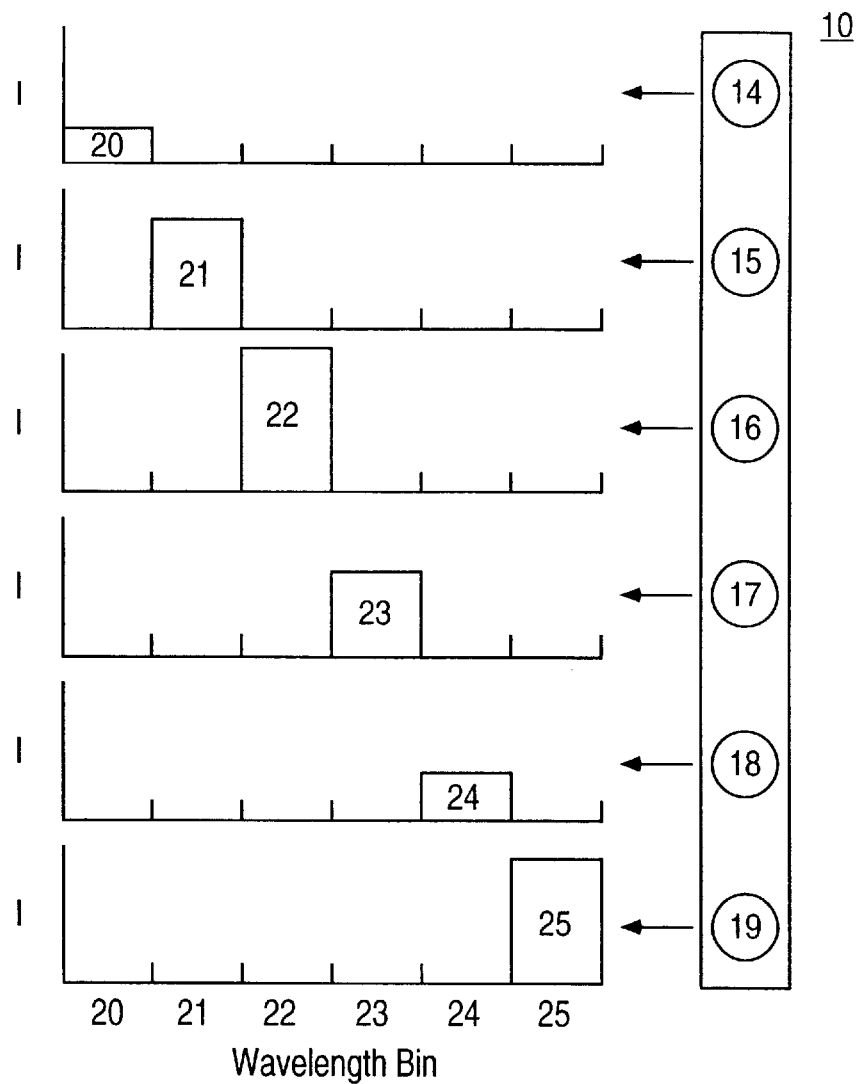
FIGS. 1a and 1b depicts detection of intensity of electromagnetic radiation simultaneously at different wavelengths, using a linear array of this invention comprising filters and detectors.

In certain embodiments, this invention includes devices and methods for using those devices for spectrographic analysis. In general, spectrographic analysis of samples can be by way of a plurality of filters and photodetectors associated with each other to detect a portion of the overall spectrum at one location relative to a sample. Other filters and detectors can be used to detect other portions of the overall spectrum from the same sample. FIG. 1 depicts a scheme illustrating certain embodiments of this invention.

Figure 1B:
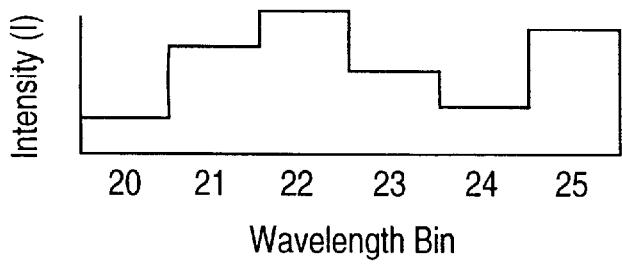

A series 10 of individual filter/detector units 14, 15, 16, 17, 18 and 19 are arrayed linearly over a sample (not shown). Each of the filter/detector units 14–19 has a different wavelength band pass characteristic. Electromagnetic radiation from the sample is collected by each of the filter/detector units 14–19 is transmitted to a display device and produces spectrographic plots of wavelength bins 20–25. Each of spectrographic plots in wavelength bins 20–25 is a graph of the intensity of detected radiation (I) on the vertical axis and the wavelength of radiation detected be each of the filter/detector units 14–19. Thus, each filter/detector unit captures a wavelength band corresponding to a portion of the spectrum obtained. FIG. 1b depicts the information shown in FIG. 1a but superimposed to show the entire portion of the spectrum obtained. As with FIG. 1a, the vertical axis displays the intensity of radiation in wavelength bins 20–25 as detected by each of filter/detector units 14–19.

Figure 2A:
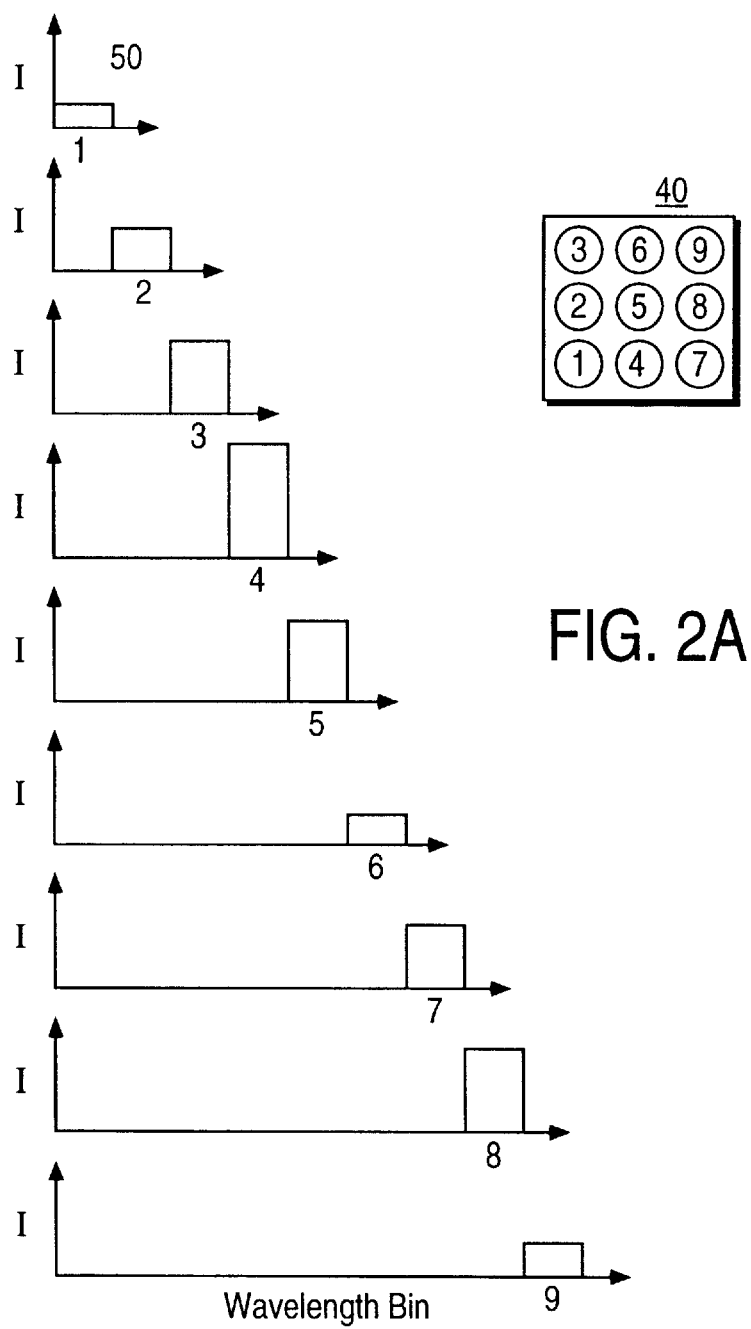
FIGS. 2a and 2b depicts detection of intensity of electromagnetic radiation simultaneously at different wavelengths, using a two-dimensional array of this invention comprising filters and detectors.
Figure 2B:
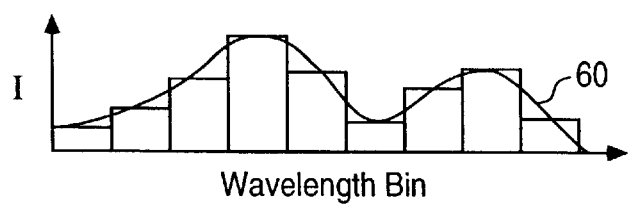

FIG. 2 depicts a scheme for obtaining spectrographic information of this invention using a two-dimensional array 40 of filter/detector units 1–9. As with FIG. 1, FIG. 2a depicts radiation captured by units 1–9 that is displayed on a series of graphs 50 of the intensity of radiation on the vertical axis and the wavelength bin captured by the filter/detector units 1–9. FIG. 2b depicts a composite spectrum of information captured by detector array 40. The spectrographic information is then expressed as a smooth curve 60, which represents an estimate of the overall spectrographic features detected.

Using these devices and methods, spectrographic information can be obtained from samples without the necessity of varying the wavelength detected over time as in conventional spectrographic analyses. Obtaining spectra is, in general, accomplished by measuring the intensity of radiation that passes through a plurality of filters, each having a different wavelength band pass characteristics. Each filter is associated with a detector that can determine the amount of radiation reaching the detector. By measuring the amount of radiation reaching each detector, the intensity of radiation at different wavelengths can be determined. By comparing the intensity of detected radiation with the wavelength band pass characteristics of the filters, a spectrum or portion of a spectrum can be obtained, and can be displayed and/or stored in electronic form for further analysis.

Acquisition of spatially resolved information can be desirable to characterize a heterogeneous sample or a cross-section of an electromagnetic beam. The use of pre-defined spatial arrangement of optical elements of this invention represents an improvement over the existing devices and methods for acquiring spectrographic information. In particular, collecting of light from a defined position onto a set of optical filters of known opacity, each filter being arranged in a pre-defined position in front of a detector, can be used for acquiring spatially resolved spectrographic information. This arrangement of elements can be used with infrared spectroscopy, fluorescence spectroscopy, surface-plasmon resonance, Raman spectroscopy or any other methods for analyzing electromagnetic radiation. In certain embodiments of this invention, microscopic analysis of samples by infrared, fluorescence, surface plasmon resonance, and Raman spectroscopy can be achieved.

In certain embodiments, radiation analyzed can include "second harmonic generation" and/or "sum frequency generation." With highly intense radiation, typically, though not exclusively achieved with laser sources, a portion of the scattered radiation can be converted into radiation having alternate wavelengths. For example, some radiation can be converted into radiation having ½ the wavelength of the incident radiation (or twice the frequency), ¼ the wavelength (4 times the frequency) or more, including the entire harmonic spectrum of electromagnetic radiation. In situations using two or more different sources of electromagnetic radiation of different wavelengths, a portion of the scattered light has a frequency being the sum of the frequencies of the incident beams. The systems and methods of this invention can be used to resolve spectrographic information deriving from either second harmonic generation of sum frequency generation.

Certain embodiments of this invention are based upon collecting electromagnetic radiation emitted from a sample and the analysis of this radiation by means of a plurality of waveguides, including but not limited to optical fibers and the like, each waveguide adapted to be directed to a particular filter in a set of filters that are spatially arranged in front of a plurality of detectors. Elements of such systems may include:

1) One or more fiber bundles, which collect electromagnetic radiation emitted from a portion of a sample and transmit this radiation to a detector;

2) A set of filters of known opacity that are spatially arranged, in accordance with the distribution of fibers in the fiber bundle; and 3) A set of detectors to determine the intensity of radiation transmitted through the filters.

These elements and systems based upon these elements are described in the following embodiments.

I. Filter/Detector Units

One feature of certain embodiments of this invention includes a plurality of filters, each of which is associated with a detector. The filter/detector units can then be placed so as to receive radiation emitted or reflected from a portion of a sample. The use of multiple filter/detector units can permit the acquisition of spectrographic information for a sample simultaneously for each wavelength being measured.

A. Filters

The quality of the spectra obtained can depend upon the wavelength selectivity of each filter and its spectrographic characteristics, and on whether and/or the extent to which spectrographic ranges for each filter overlap with each other. Filters that are useful for certain embodiments of this invention can have a relatively narrow band of wavelengths that can pass through each specific filter. Among various existing filters, liquid crystal tunable filters can be particularly useful for allowing passage of light of selected, relatively narrow wavelength ranges. These filters can provide highly selective and tunable opacity via orientation of molecules in a liquid crystal in response to externally applied electric fields. The manufacturing of these filters is well known in the art and is described in the patent titled "Tunable wavelength-selective filter and its manufacturing method", inventors: H. Takayoshi, et al., European Patent Number: EP0903615, publication date: Mar. 24, 1999. This patent is herein incorporated fully by reference.

Other types of filters can be used, for example, including plastics or glasses that are doped with compounds or mixtures of compounds that absorb substantially all radiation with the exception of a desired band of wavelengths. These filters can be individually placed over a corresponding individual detector to form a filter/detector unit.

B. Transmission of Electromagnetic Signals to Detectors

The basis for detection by devices and methods of this invention is the acquisition and characterization of electromagnetic radiation from the sample under analysis. For convenience, the term "light" herein is intended to include electromagnetic radiation outside the visible range, and can include gamma-ray, x-ray, ultraviolet, visible, infrared, and radio frequency radiation. Similarly, the term "optical" as used herein includes electromagnetic radiation within and outside the visible range of wavelengths. Thus, in situations in which the spectrographic information is within the visible range of wavelengths, the term "optical" and "light" have their usual meanings, and when the spectrographic information is outside the visible range, the terms "optical" and "light" are used for convenience only, and are not intended to be limiting to the scope of this invention.

When the tip of an optical fiber is positioned relative to a surface of an object, radiation emitted from this area can be collected by a waveguide. As used herein, the term "waveguide" means a device that guides electromagnetic radiation in a particular path. Waveguides include light pipes, optical fibers and other devices through which radiation can be transmitted. Waveguides can have circular, square, hexagonal triangular or other cross-section shapes. A plurality of waveguides can be arranged in a bundle and can be fused together. Waveguides can be manufactured for a specific use or can be purchased commercially (e.g., Collimated Holes, Inc., Campbell, Calif.). Commercial waveguides can have diameters as small as 1–3 $\mu$m, but any desired diameter can be made using methods known in the art. The lower limit of diameter is related to the wavelength of electromagnetic radiation that can be transmitted through the waveguide with a desired degree of efficiency. For example, waveguides having diameters of about 0.5 $\mu$m can be used for certain visible and ultraviolet wavelengths, waveguides having diameters of about 0.1 $\mu$m can be useful for certain deep ultraviolet ("vacuum ultraviolet") and waveguides having diameters of several Å can be used for capturing soft X-ray radiation. For most purposes herein, the terms waveguide, optical fiber, and light pipe have the same meanings unless specifically defined differently for particular applications. In certain embodiments, radiation can be collected directly by a waveguide. However, in certain other embodiments, it can be desirable to focus the radiation onto the waveguide by a lens or other device. The configurations of sample, surface, waveguides, and/or lenses can be varied to suit the particular needs of the analysis. In certain embodiments, focusing devices such as lenses can incorporate filters. In other embodiments, a focusing device can be a separate element.

The analysis of the light by means of dispersion or a filter set can be used to characterize the spectrum of the collected radiation. By scanning the tip of the optical fiber over the whole surface, spectroscopic characterization of the whole object can be obtained. Radiation can be transmitted to a remote detector. A filter can be placed at either end of the waveguide, and in some embodiments, the waveguide can comprise an optical fiber incorporating a filter, eliminating the necessity of having separate filter and waveguide. Additionally, detectors can be sensitive to a particular range of wavelengths, and thus, eliminate the need for a separate filter.

In yet other embodiments, filter, focusing device and waveguide can be separate elements. In these types of embodiments, it can be possible to change the configuration of waveguides separately from filters, permitting replacement of waveguides that may have become damaged or are otherwise defective. Moreover, one can change the filter associated with a particular waveguide to alter the wavelength transmitted by that waveguide to a detector.

In certain embodiments, it can be desirable for optical fibers to be sufficiently small to permit the use of a plurality of fibers simultaneously over a relatively small sample, such as a sample of analyte on a biochip. Such a plurality of fibers is herein termed a "fiber bundle." The term "biochip" as used herein means a substrate onto which an analyte of biological interest (herein termed a "bioanalyte") is present. Such analytes include but are not limited to nucleic acids (e.g., DNA, RNA), nucleotides, nucleosides, proteins, peptides, amino acids, nucleic acid/protein associates, low molecular weight molecules (e.g., vitamins, sugars and the like), bacterial toxins, enzymes, co-factors, and the like. For example, for a bioanalyte application of this invention, if a sample is represented as a square having sides 1 mm long each, the area of the sample will be 1 mm$^2$. Optical fibers 0.5 mm in diameter can permit the use of four fibers arranged in a square, and can detect signal from the sample, with less than about ¼ of the total area being observed by each fiber. Optical fibers 0.1 mm in diameter can be arrayed in a square comprising 100 fibers, 10 per side, each of which can observe less than about 1/100 of the total sample. Optical fibers 0.01 mm in diameter can permit the simultaneous observation of the same sized sample (1 mm$^2$) by 10,000 individual fibers, 100 per side, as arranged as a square, each observing less than about 1/10,000 of the total area of the sample. By associating each fiber with a filter having a different wavelength band pass range and/or mean, it is possible to obtain 10,000 individual measurements at 10,000 different wavelengths simultaneously. In other embodiments, the fiber diameter can be reduced to about 1 μm or lower. Optical fibers of such diameters can permit the simultaneous detection of 1,000,000 points on the sample. If, for example, 1000 individual wavelengths are to be measured, then about 1000 individual measurements can be made at each wavelength. Such replicate measurements can be averaged if desired to estimate the intensity of radiation at each wavelength. Other densities can be used and is limited only by the packing density and the efficiency of transmission of radiation through the waveguides suitable for collection of radiation of desired wavelengths. The above is intended for illustration only, and is not intended to limit the scope of this invention.

The above descriptions relating to square arrangements of fibers is for illustration only, and is not the only arrangement possible. Circular, other curvilinear, triangular, square hexagonal or linear arrangements are within the scope of this invention. We note that with triangular or hexagonal packing of circular fibers, the density of fibers in such fiber bundles is increased compared to square packing. Additionally, bundles of hexagonal, square, or triangular fibers can be placed, such that individual fibers can abut or be positioned near one another and provide a desired total area of coverage. If individual fibers are close together, then the spaces between them can be minimized and the total area from which radiation can be captured can be increased. Thus, by the use of a sufficient number of fibers, a large portion of a spectrum of radiation emitted by the sample can be constructed by presenting the individual data points in a display as described above.

Waveguides or fibers can either be made according to particular needs of diameter, length, and material. Alternatively, fibers and/or fiber arrays can be obtained from Collimated Holes, Inc., Campbell, Calif. Fibers can be obtained that are square, rectangular or circular, and can provide up to about 90% core area (90% coverage), and can have sizes of individual fibers about 25 μm in diameter. However, fibers with smaller sizes can be made to suit particular purposes. The only requirement is that the fiber be sufficiently large to transmit the wavelength of radiation sufficiently well to be detected and/or quantified by the photodetector.

In other embodiments, it may be desirable to use fibers of different diameters in the same bundle. For example, for fibers having circular cross section, even a hexagonal packing array leaves gaps between the fibers. By interspersing fibers of smaller size, more of the sample are can be observed. As long as the intensity of the signal is corrected for the cross-sectional area of its acquisition, the use of mixed sized fibers presents no substantial difficulty or limitation to the use of the devices.

In certain situations, when it is not necessary to detect and/or record the entire spectrum, one can select portions of the spectrum and use only those waveguides and filters necessary to obtain the desired spectrographic information. For example, in a situation in which 10,000 individual wavelengths are sufficient to capture a complete spectrum, if about 1/10 of the total spectrum is desired, one can either duplicate measurements at one or more individual wavelengths, or can reduce the total number of fibers used, thereby permitting reduction in the size of the sample to be detected. In this situation, the total sample size can be 0.1 mm$^2$, and permit the acquisition of spectrographic information of similar quality to the information captured by an array of 10,000 fibers measuring a 1 mm$^2$ area of sample.

In designing fiber arrays, it can be desirable to consider the loss of signal through the fiber after its acquisition by the fiber. It can be desirable to minimize signal loss by keeping the total length of the fibers within certain limits, depending upon the acceptable loss of signal. Additionally, the material used should be compatible with acceptable signal losses. In general, it can be desirable to make fibers with materials having high transmittance to the wavelengths to be analyzed. However, as long as the transmission characteristics of the fibers are known, it is possible to correct results (or "standardize") the assays to take such losses into account. Such corrections can be desirable if the transmission characteristics of the fibers differs according to the wavelength of radiation.

A significant drawback in the use of conventional filter-based devices for acquisition of spectra is the necessity to collect data point-by-point. When there is a need to collect data over a broad spectrographic range, obtaining spectrographic data can take a long time. In contrast, by using devices and methods of this invention, one can obtain spectrographic information at a plurality of different wavelengths simultaneously, thereby increasing the speed of data acquisition.

C. Photodetectors

In certain embodiments of this invention, photodetectors can comprise photographic film, photodiodes, photomultiplier tubes (PMT), charge coupled devices (CCDs) and/or any other devices known in the art. In certain situations, it is desirable to use photodetectors that are sufficiently small so as to permit the use of multiple detectors simultaneously. In certain embodiments, a plurality of photodetectors can be provided having a either square, triangular or hexagonal planar array. In such situations, the fiber bundles can have individual fibers of approximately equal length. In these embodiments, the geometrical array of the tips of the optical fibers over the sample can be re-created by a geometrical array of detectors. In this situation, there is a 1:1 two-dimensional mapping of the optical fibers onto the photodetector array.

In other embodiments, it can be desirable to provide optical detectors out of plane with each other. In these situations, the packing density of the detectors need not be as limiting to the number of detectors is in situations in which the detectors are in a planar array. Thus, optical fibers need not be of approximately equal length, and a fiber bundle, detector package can be manufactured in which a two-dimensional surface of a sample is mapped onto a three-dimensional structure of detectors. This can permit the acquisition of more data points (and therefore more wavelengths) than practical using two-dimensional detector arrays.

The types of detectors is not necessarily limiting. Any suitable detector that can capture and quantify electromagnetic radiation can be used with the devices and methods of this invention. Film, diode detectors, CCDs can be used. However, it can be desirable to use CCD devices. Charge coupled devices can be made or obtained commercially that have sizes that are compatible with measuring relatively small areas and relatively low intensities of radiation that characterize some spectrographic features to be detected. Advantageously, one can use a plurality of identical detectors to acquire an area-average spectrum, and thereby can diminish problems associated with different efficiencies of radiation capture by different waveguide/filter/detector units. Alternatively, the sample can be moved under the detectors, and spectrographic information can be acquired from different areas and averaged to achieve the spectrum. Moreover, using electrically coupled detectors permits the easier manipulation of data after its capture.

Signals from the photodetector can be transmitted to a computer, where a program can be used to standardize the signals and to create plots of spectrographic features, determine the total intensity of the features, and perform other calculations. The signals can also be stored in a memory device for further processing or comparison at a later time.

II. Detection using a Microscope or Other Optical Devices

Microscopes can allow observation of small objects, but spectrographic analysis of light emitted from a particular area of such objects represents a challenge. In certain conventional approaches, radiation is directed, by fibers arranged in line, onto the entrance slit of a spectrograph. A detector, such as a CCD is positioned at the exit slit of the spectrograph. The dispersed light from each fiber is detected and addressed so as to allow one to address each fiber with its spectrum. An image of the object is obtained by computer analysis. Such acquisition of spectra from a surface is well known in the art (see for example article by McClain et al., entitled Fast Chemical Imaging, Spectroscopy 15 (9), 28–37 (2000), incorporated herein fully by reference). However, the need for a spectrograph makes this approach expensive.

In certain embodiments of this invention, to obtain spectrographic information from a small area, a near-field approach can be used without lenses or other focusing mechanisms. A small bundle of waveguides can be positioned close to a small area to be assayed. Measurements can be obtained at a plurality of different locations within the sample. By "scanning" the probe tip or bundle across the surface of the sample, spectrographic information can be obtained from discrete areas, stored, and can be analyzed for differences between areas, or alternatively can be averaged to obtain overall spectrographic information for the sample.

Alternatively, a microscopic image formed using a conventional microscope having lenses or other focusing mechanism can be projected onto an array of filter/detector units, and simultaneous analysis of radiation from individual elements of this array can be performed.

In addition to microscopes, telescopes can be used to collect radiation for spectrographic analysis using the devices and methods of this invention. For example, electromagnetic radiation collected from an optical telescope can be detected using a series of filters and detectors to obtain spectra of astrophysical phenomena, including stars, galaxies, quasars, planetary bodies, asteroids and the like.

III. Analyte Detection

In certain embodiments of this invention, analytes can be detected without separation from other analytes and/or materials. Such identification can be carried out if the analyte has a specific or unique spectrographic feature that can be used to identify and/or quantify the analyte. In other embodiments of this invention, detection of an analyte not having a unique spectrographic feature can be accomplished by selecting the analyte from among a number of other species having a similar spectrographic feature, using, for example specific binding of the analyte to an analyte receptor. For example, a specific DNA species can be selected by permitting that DNA species to bind to a complementary DNA or RNA receptor on a substrate such as a biochip. Similarly, small molecule analytes can be selected for analysis by use of specific receptors for those analytes. By way of example only, detection of glucocorticoids can be accomplished by using glucocorticoid receptors. By analogy, other receptors having specifically binding to analytes can be used to select for those analytes.

In general, a substrate can be prepared with a number of receptors for a desired analyte placed in an area on the substrate. A test sample containing the analyte can be applied to the surface, where some of the analyte can attach to the analyte receptor. Then detection of the analyte can be accomplished. In situations in which the analyte has a characteristic spectrographic feature, the detection of that spectrographic feature can indicate the presence of the analyte on the substrate.

To quantify the amount of analyte, a first spectrum can be obtained for the substrate with the attached receptors. The resulting spectrum is herein termed a "blank" or "negative control." This spectrum can be stored in a memory device for comparison with other spectra. Then, a spectrum can be obtained of the same area of substrate but after attachment of the analyte to the receptors. This spectrum is herein termed an "unknown" spectrum. It is apparent that one or more such "unknown" spectra can be obtained, wherein different amounts of analytes are attached to the receptors. In general, if more analyte is bound to the substrate, the intensity of the spectrographic signal will be larger than situations in which less analyte is bound. By performing studies using different amounts of analytes, the threshold sensitivity of the method, the concentration response relationships, and the maximum detectable limits can easily be determined using standard methods known to those skilled in the analytical arts.

After a desired number of unknowns have been assayed, the substrate can be treated to remove the attached analytes, and additional spectrographic measurements can be obtained. Desirably, when all of the analyte has been removed from the substrate, the observed spectra are substantially the same as the spectra obtained from the same area of substrate but prior to attaching analyte thereto.

IV. Array Readers

Certain embodiments of this invention can be used to read an array of different samples on a substrate. Arrays of samples can be conveniently prepared using methods known in the art. For example, a DNA chip is a surface having well defined areas called spots or cells, onto which analytes are retained via binding to receptors attached at these reas. Because each spot has its own well-defined position on the DNA chip surface, these DNA chips can be called DNA arrays. The intensity of light emitted in a particular spectral range serves for the detection of the amount of an analyte retained at each spot. Among a large variety of chemically heterogeneous objects that require characterization by means of a spectroscopy, those DNA chips can present a peculiar situation: On one hand, these areas can be small and require a microscopic device for their observation. On the other hand, the precise position of each spot makes it unnecessary to scan the whole surface of the chip. Conventional DNA chip readers are expensive and, in general, analytes are labeled with fluorescent tags and then are detected by the fluorescence.

Array readers according to this invention can include readers of single samples, two by two arrays of samples, linear arrays of samples, or in any other desired configuration.

V. Raman Spectroscopy and Microscopy

Raman spectroscopy can be particularly useful for characterizing matter including bioanalytes, because it can be performed without the necessity of providing a label on the material to be analyzed. Raman spectroscopy is based upon interaction of incident electromagnetic radiation with intrinsic electromagnetic field fluctuations that can arise from intra-molecular movements or vibrations. The interaction between incident and emitted radiation can be diagnostic of specific materials in that most materials scatter electromagnetic radiation in very specific ways to produces a Raman signal. Acquisition of Raman spectra from various parts of an sample can provide valuable information on the composition of the sample. At present, such spectral and spatial information is obtained in Raman microscopy by collecting images of the object through a set of filters, one filter at a time.

One problem that has limited the use of Raman spectroscopy is that, in general, Raman signals from most materials is weak. Two generally applicable approaches for signal enhancement are put forward. One approach relies upon enhancement of Raman signal by roughen metal surfaces and is known as "surface enhanced Raman spectroscopy" or "SERS." This approach can be useful for detection of analytes in the presence of such surfaces, which include factual structures. Additionally, Raman signals can be further amplified by using receptors bound to Raman enhancing structures, such as factual structures. Such systems and methods are described in co-pending U.S. Utility patent application Ser. No: 09/670,453, filed Sep. 26, 2000 entitled: "Nanoparticle Structures with Receptors for Raman Spectroscopy" Kreimer et al., inventors, incorporated herein fully by reference. As described in the above visional patent application, a passivation agent such as mercaptobexanol (1 mM can be used to eliminate non-specific binding Another approach utilizes the enhancement of electromagnetic radiation within cylindrical or spherical microcavities, hollow tubes or other optical resonators. This approach is called "morphology dependent resonance" or "MDR." MDR Raman spectroscopy is described in co-pending U.S. Utility patent application Ser. No: 09/669, 369, filed Sep. 26,2000, entitled: "Addressable Arrays Using Morphology Dependent Resonance for Analyte Detection," Yevin et al., inventors, incorporated herein fully by reference. Detectors, array readers, systems and methods for spectrographic analysis of this invention can be advantageously used with the methods, devices, and substrates described in the co-pending patent applications.

In addition, resonance Raman spectroscopy can be used, in which the wavelength of excitation radiation overlaps an absorption band of an analyte. This can be combined with SERS and/or MDR. Multiphoton excitation can also be used, wherein two or more photons having relatively low energy are used to achieve an overlap with an absorption band of an analyte.

The above-described methods for acquisition of spectra of electromagnetic radiation emitted from particular areas of objects or through a cross-section of an electromagnetic beam can permit one to characterize simultaneously spatial and spectral distribution of the intensity of electromagnetic radiation. It can be desirable to obtain such information rapidly, such as high throughput analysis of bioanalytes using biochips, control for the process of manufacturing various microscopic and macroscopic objects, and/or monitoring of pollution from an aircraft.

VI. Addressable Array Readers

In certain embodiments of this invention, it can be desirable to provide spectrographic analysis of a plurality of samples on a single substrate. Such substrates having a plurality of samples thereon are herein termed "addressable arrays." In certain embodiments, addressable arrays can be present on substantially planar substrates, and these "biochips" can have samples thereon in places that can be predetermined during their manufacture, or can be determined after manufacture by the detection of a tag or marker specific for the position on the addressable array.

Certain embodiments can advantageously use conventional two-dimensional biochips, for example, those containing DNA, protein, or collections of small molecules, including libraries of compounds for drug development. For two-dimensional arrays, the position of each of a plurality of samples can be addressed using X and Y coordinates. The positional information can be stored in a memory device, and a reader controller can move a probe to the address of the sample for measurement of spectrographic information. A reader probe can be attached to a moveable arm that can be under servo control by the user or, alternatively, a computer. After a sample address is selected, the probe and arm can be moved to that position, the probe can be placed in position relative to that address, and spectrographic information collected and stored. After a measurement is made, the probe can be moved to another addressable location and spectrographic information can be collected for that sample. In this way, a plurality of samples can be placed in an addressable array, and repeated measurements can be made of one or more samples.

In certain other embodiments, an address on an array can be by way of a marker or tag placed along with the sample on the substrate. Such markers can include color coding, in which each column and can be represented by a different color. Thus, for each address on the substrate, a unique combination of two colored materials can be provided. Detection of the colors in the sample locations can provide a desired system for relating spectrographic information to a sample's address. Color detectors are known in the art and need not be described further.

Alternatively, unique molecules can be used as positional markers. By providing markers having unique characteristics that can be determined, positional identification can be correlated with spectrographic information recorded by the filter-based spectrographic apparatus of this invention.

For color-based and chemically based identification, it can be desirable for the marker to be detectable using a feature that does not interfere with the spectrographic analysis of the sample under study. For example, if samples are analyzed using Raman spectroscopy, markers having Raman spectra that do not interfere with the sample's spectrum can be used. Moreover, fluorescent labels can be used if the wavelengths of fluorescent emission do not interfere with the acquisition of spectral information of the sample. Numerous combinations of sample variables and marker variables can be chosen and be within the scope of this invention.

In certain other embodiments, samples can be arrayed in a one-dimensional array. In certain of these embodiments, a flexible substrate can be provided with a source reel and a take-up reel. The substrate can be a long piece of material having a longitudinal axis. Samples can be placed on the substrate in a linear array, and as more samples are added to the substrate, the take-up reel can store collected samples. The source reel can provide additional substrate for application of additional samples. In this fashion, a plurality of samples can be collected and brought to a reader, for example, a "strip reader" for analysis as described below.

It can be appreciated that a one-dimensional array of samples can have individual samples with circular configuration, oblong configuration, or any other desired configuration. In certain embodiments, a sample can have an approximately rectangular shape, having a longitudinal axis and a minor axis. The longitudinal axis of a sample can be oriented non-parallel to or approximately perpendicular to the longitudinal axis of the substrate strip. A plurality of samples can be stored and read using a linear array of filter/detector units and can conserve space on the substrate. It can be appreciated that other orientations of samples on a substrate can be used without departing from the scope of this invention.

By using either a positional address or an address-specific marker or tag, the spectrographic information collected can be stored along with information about the position of the sample on the array or an associated marker or tag. Such information can be annotated to include other information about the sample, including but not limited to time of collection, type of sample, source of sample, conditions of pretreatment of the sample and a wide variety of other information. Collation of information concerning a sample and the sample's spectrographic information can provide a powerful tool for analysis of samples and development of new information.

VII Protection of Information

In other aspects of this invention, the systems and methods of this invention may yield valuable proprietary information and/or personally identifiable information whose management, transmission, use and/or disclosure may be at least in part regulated by laws, rules, and/or regulations of one kind or another, including, for example, the U.S. Health Insurance Privacy and Accountability Act of 1996 ("HIPAA"), (PL-104-191 and rules and regulations thereinunder) and similar laws, rules and regulations.

In one embodiment of this invention, to maintain security, privacy, confidentiality, and/or control over the results obtained, it can be desirable to incorporate software and/or hardware for digital rights management ("DRM"). In general, DRM technologies can associate rules governing authorized use of digital information and consequences of such authorized use, including audit and/or usage record creation, aggregation, and/or reporting, with digital information (regardless of format). Digital information can be protected at least in part by encryption. Rules and/or protected information may be stored and/or transmitted in a secure software "container" or hierarchical encrypted file structure. Secure software container may be created and/or its contents accessed only by a trusted computer space ("TCS"). A TCS may comprise tamper resistant hardware and/or software. A TCS may be at least in part integrated into an operating system that provides services to, and may also at least partially control the trusted device.

Certain TCS embodiments are based on technologies currently available. For example, in one embodiment, InterTrust Technologies Corporation provides TCS described in U.S. Pat. Nos: 6,157,721, 6,138,119, 6,112,181, 5,982,891, 5,949,876, 5,920,861, 5,917,912, 5,915,019, 5,910,987, 5,892,900 and WIPO Publications WO 9,810,381 A1 and WO 9,901,815 A1, each publication incorporated herein fully by reference.

Certain other commercial embodiments include available DRM technology of ContentGuard, Inc. described in U.S. Pat. Nos: 5,715,403, 5,638,443, 5,634,012, 5,629,980, each publication incorporated herein fully by reference. Other DRM technology of MediaDNA described in U.S. Pat. No: 5,845,281, incorporated herein fully by reference.

Trusted computing space is a secure, tamper resistant software and/or hardware component that incorporates a protected computing environment ("PCE") for evaluation and enforcement of rules governing authorized use and access of protected information. In some embodiments, the TS manages a protected data area ("PDA") which may, for example, comprise one or more encrypted files on a local PC disk drive and/or may occupy a portion of solid state memory. In one example, a PDA may be used to store cryptographic information, rules governing authorized access, digital credentials, information documenting authorized use, and in some embodiments, payment, budget, and/or other financial information. One embodiment of the present invention includes a commercially available InterRights™ Point software from InterTrust Technologies Corporation. In certain embodiments, the TCS may be incorporated into specialized hardware in the form of a controller chip for peripheral or other devices. One embodiment includes the RightsChip, now commercially available from InterTrust Technologies Corporation and related to the InterTrust pending and/or issued patent applications cited herein.

In certain embodiments, spectrographic analysis system with incorporated TCS can protect information upon or near to its creation. Thus, spectrographic information so obtained and stored can be protected from unauthorized use and access and/or can document the circumstances of authorized use. One benefit of incorporating DRM technologies into the systems of this invention is that the valuable proprietary and/or personally sensitive information can be protected for integrity and against unauthorized use from the time of or near its creation.

In certain embodiments, an AC-DC converter, a memory device, and/or a computer can incorporate TCS devices. In some embodiments, a display device can also incorporate a TCS device. In certain of these embodiments, only one of the above devices incorporates a TCS, whereas in other embodiments, a plurality of the above components incorporate TCS devices. In those systems that incorporate multiple TCS devices, the TCS devices may exchange encrypted spectrographic information and/or rules associated with said information. Spectrographic information may be transmitted to external systems in cryptographically secure containers. One embodiment of a secure container is a DigiBox® secure software container that is part of a DRM software platform commercially available from InterTrust Technologies Corporation and related to the InterTrust pending and issued patents cited herein.

Those skilled in the art can create applications, solutions, and services that incorporate digital rights management technologies that can protect data created by the filter-based spectroscopic analysis systems disclosed herein for integrity and against unauthorized access and use.

EXAMPLES

The examples that follow are intended to illustrate embodiments of this invention, and are not intended to limit the scope of the invention. For instance, several examples depicted below include focusing devices such as lenses. Many of the embodiments are contemplated that do not necessarily use focusing devices. Moreover, the substrates depicted are for illustration only, and other types of sample configurations are contemplated.

Example 1

Fiber Bundle

Figure 3A:
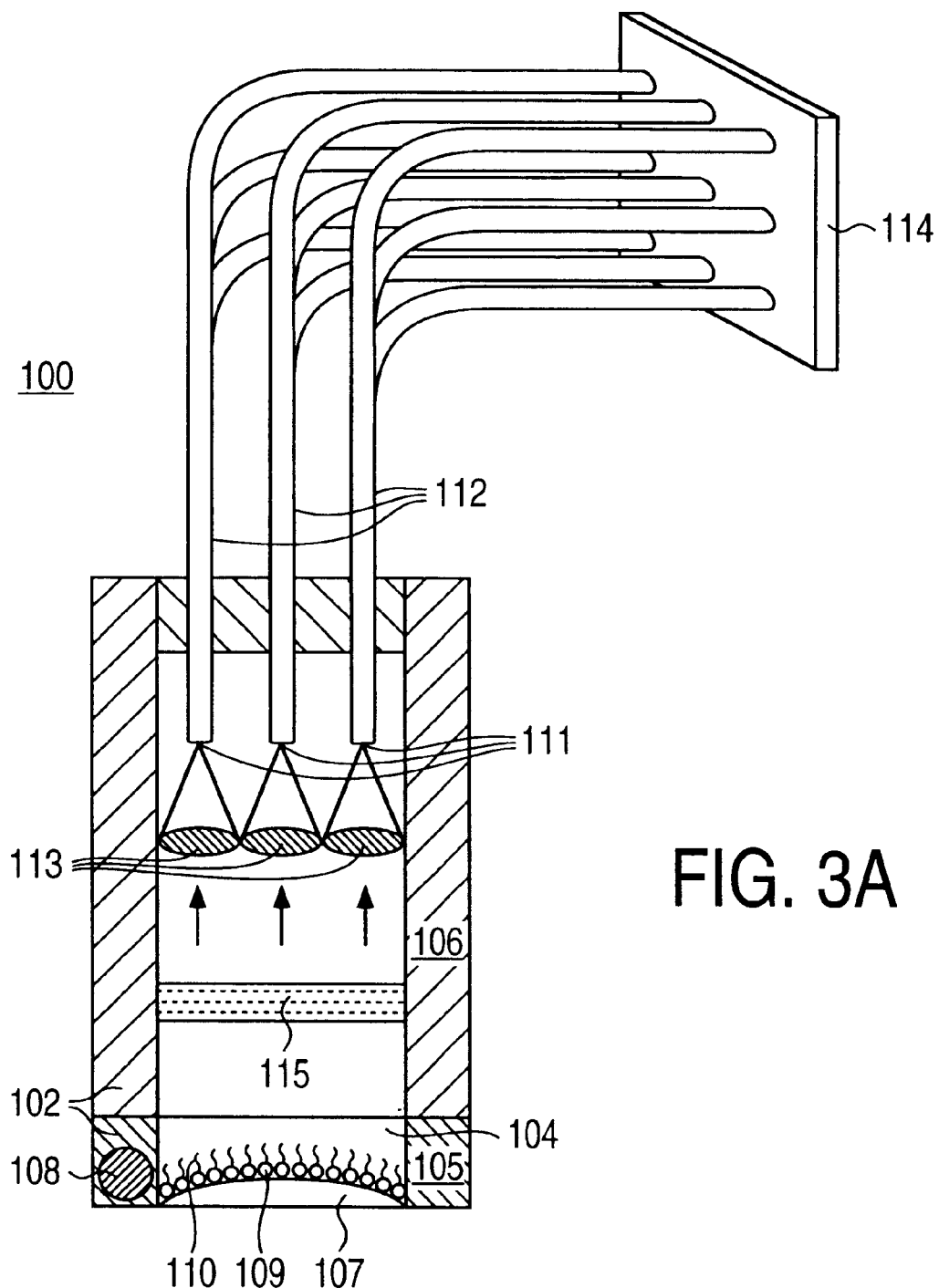
FIGS. 3a–3b are drawings depicting an embodiment of this invention for the collection of electromagnetic radiation from a sample.
Figure 3B:
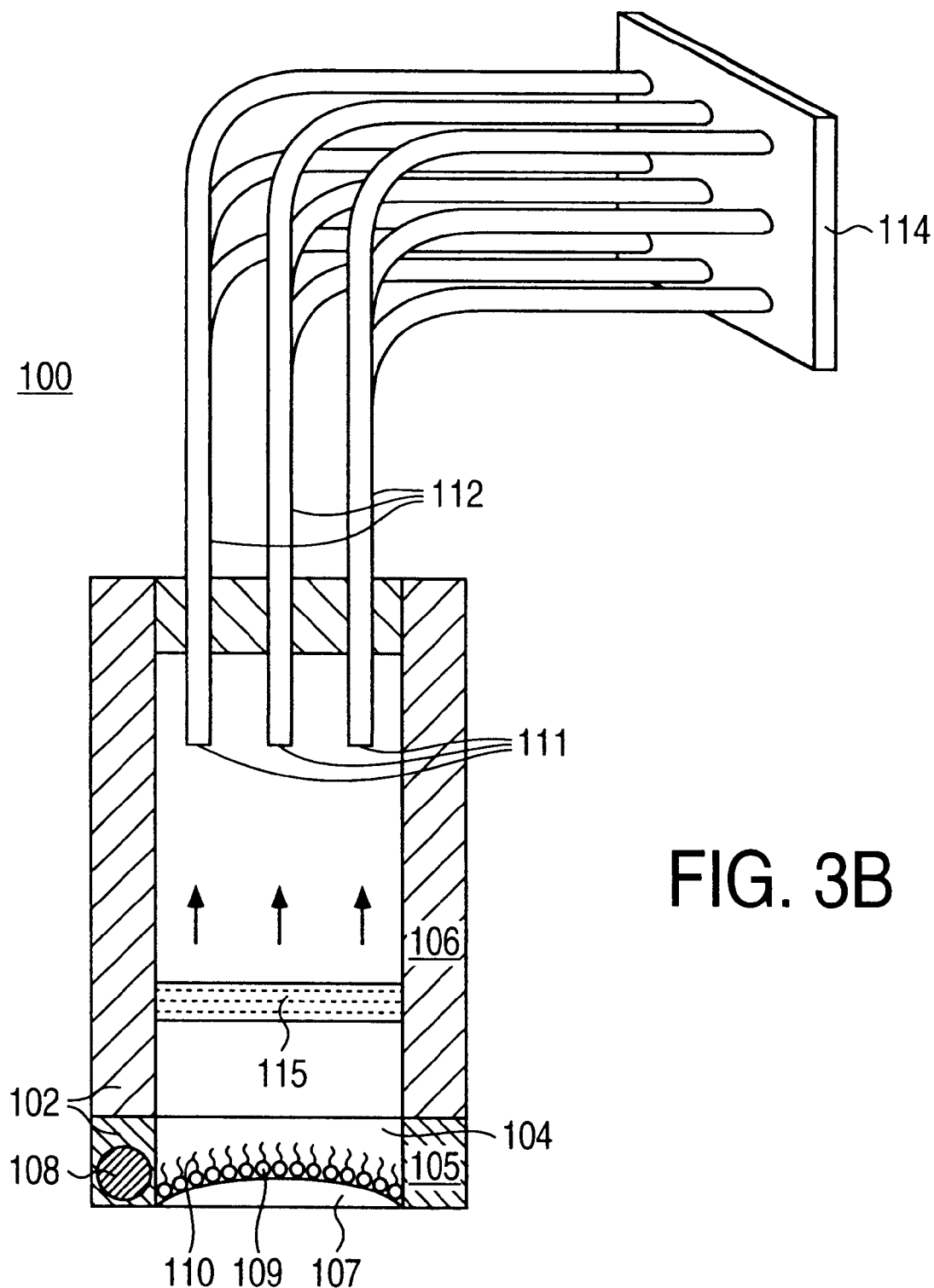

Referring to FIG. 3a, one embodiment of this invention is a directed fiber bundle probe 100 for collecting light from a small area or space 104 illuminated via fiber 108 and directing the collected radiation by means of a bundle of fibers 112 and lenses 113 arranged by fiber collector 114. It can be desirable to arrange head 102 of the probe in the shape of a cylinder, which can allow one to achieve an MDR condition for illumination. Head 102 can be made of two materials, top part 106 being non-transparent to avoid the loss of signal light within the fiber and to minimize the acquisition of parasite light, and bottom part 105 being made of glass or quartz, to provide MDR conditions. Illumination of area 104 under MDR conditions can result in an increase of the intensity of electromagnetic field within this area. The probe can be used for collecting radiation emitted from area 104 as the result of illumination of that area by an incident electromagnetic radiation or by emission of electromagnetic radiation from this area due to any other phenomena. FIG. 3b depicts an embodiment of this invention similar to that shown in FIG. 3a having no lenses 113.

FIG. 3 also illustrates one use for probe 100. FIG. 3 depicts the collection of Raman and/or fluorescence signals from analyte 110 bound to receptor 109, which is attached to SERS-active substrate 107. Upon excitation of The signal, total light emitted from area 104 passes through notch filter 115 to cut off the excitation light and prevent its capture by optical fibers 111. Radiation passed through the filter is collected onto entrances 111 of optical fibers 112 by lenses 113.

Example 2

Alternative Fiber Bundle I

Figure 4:
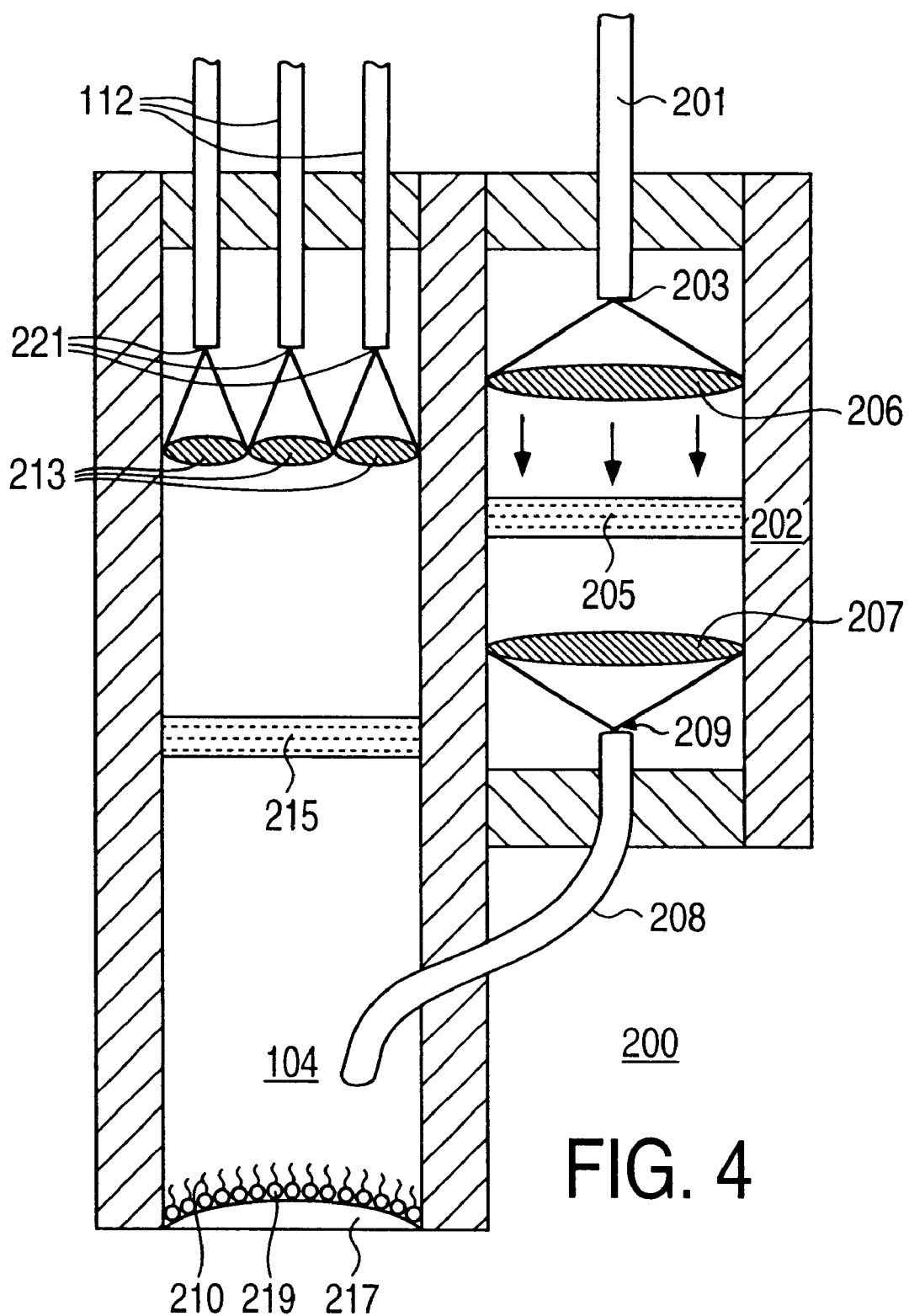
FIG. 4 depicts another embodiment of this invention where illumination of the area under analysis is performed using waveguides.

FIG. 4 illustrates another embodiment of this invention, a fiber bundle probe 200 for collecting light from a small area or space 104 illuminated via fiber 208 and directing the collected radiation by means of a bundle of fibers 212 and arranged by a fiber collector (not shown). This probe 2 can be used for collecting radiation emitted from the area as the result of its illumination by an incident electromagnetic radiation or due to emission of electromagnetic radiation from this area 104 due to any other henomena.

Illumination of area 104 is achieved by using light directed from a remote light source via fiber 201: Light coming into excitation-light transmitting compartment 202 via fiber 201 is collected from tip 203 of fiber 201 by lens 206. Upon passage through an optical filter (which can be a notch or a holographic filter transparent only for a desirable excitation wavelength) 205, narrow wavelength band of light is collected by lens 207 onto tip of 209 of fiber 208. FIG. 4 depicts the collection of Raman and/or fluorescence signal from analyte 210 bound to receptor 219, which is attached to SERS-active substrate 217. Upon excitation of the signal, total light emitted from area 104 passes through notch filter 215 to cut off the excitation light. Radiation passing through the filter is collected onto entrances 221 of optical fibers 212 by lenses 213. The signal collected from area or space 104 is the sum of signals brought to a detection device by fibers. These fibers collect portions of the signal from sub-areas determined by collection lenses of such probes. It can be desirable to use several fibers for bringing radiation to the same device for detection of electromagnetic radiation in only particular wavelength range. The use of a plurality of fibers (3 to 10 fibers for one wavelength range) can be sufficient to minimize problems associated with dependence of collected spectra upon geometry. In certain embodiments, instead of having several fibers bringing information from several sub-areas, vibration or rotation of a sample or a probe can be used to avoid the geometric dependence.

Example 3

Alternative Fiber Bundle II

Figure 5:
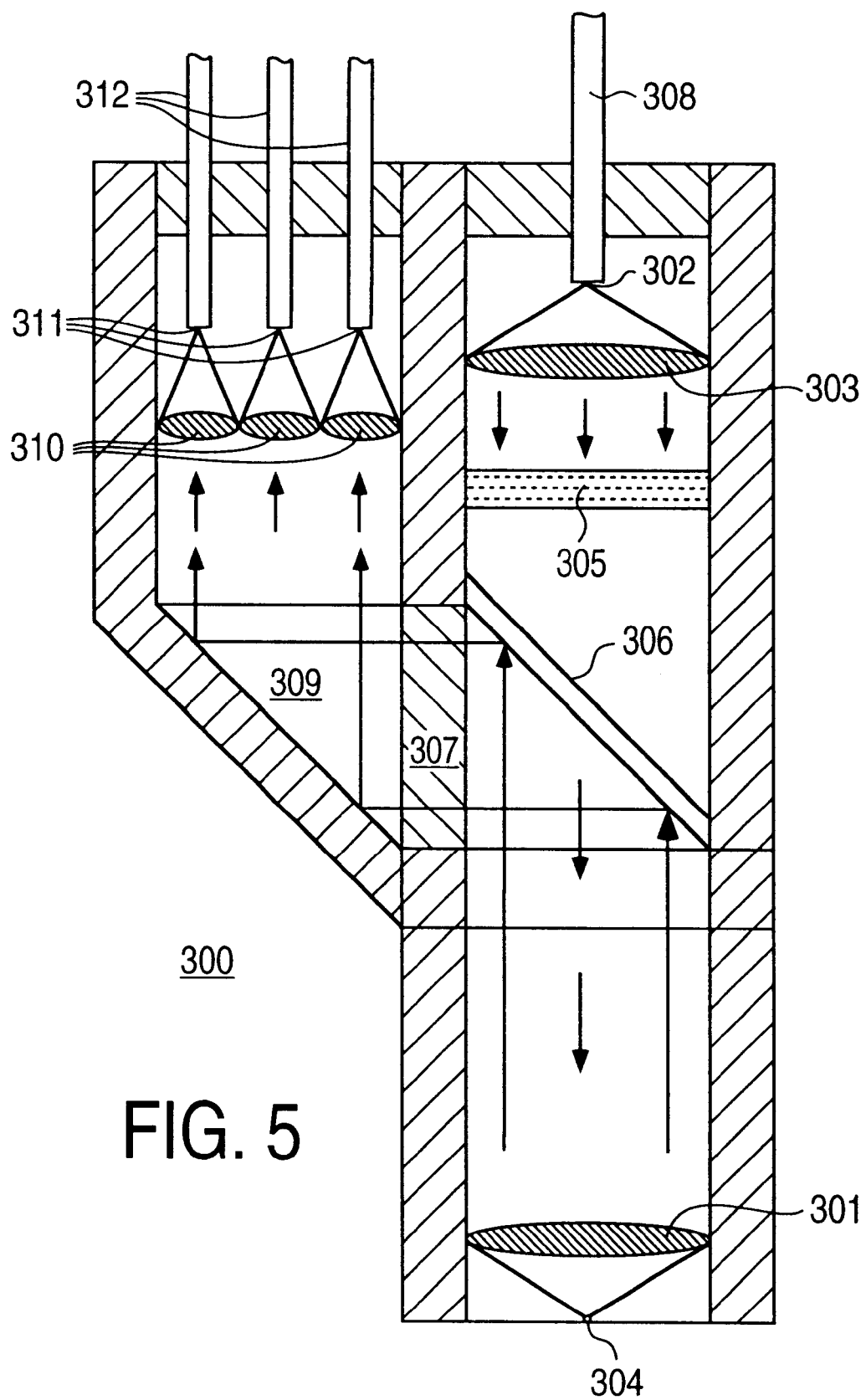
FIG. 5 depicts an embodiment of this invention for the collection of electromagnetic radiation from a sample using a focusing system.

FIG. 5 illustrates another embodiment of this invention, a fiber bundle probe 300 for collecting light from a microscopically small object 304. Illumination of object 304 is achieved by light transmitted from a light source (not shown) via fiber 308. The tip 302 of fiber 308 is in the focus of lens 303. Upon passage through filter 305 (which can be a notch filter or a holographic filter transparent only for a desirable excitation wavelength), a parallel beam of excitation light, upon passage trough a semi-transparent mirror 306 is focused onto object 304 by lens 301. Radiation emitted from object 304 is focused into a parallel beam by lens 301, reflected by semitransparent mirror 306, directed onto notch filter 307, and upon passage through this filter, is directed by prism 309 onto a set of lenses 310. These lenses 310 focus the beam onto tips 311 of fibers 312. The opposite tips of these fibers 312 are arranged via a fiber collector (not shown).

It can be desirable to use a focusing objective composed of several optical elements instead of lens 301 for better spatial resolution.

Example 4
System for Filter-Based Spectroscopic Characterization

Figure 6:
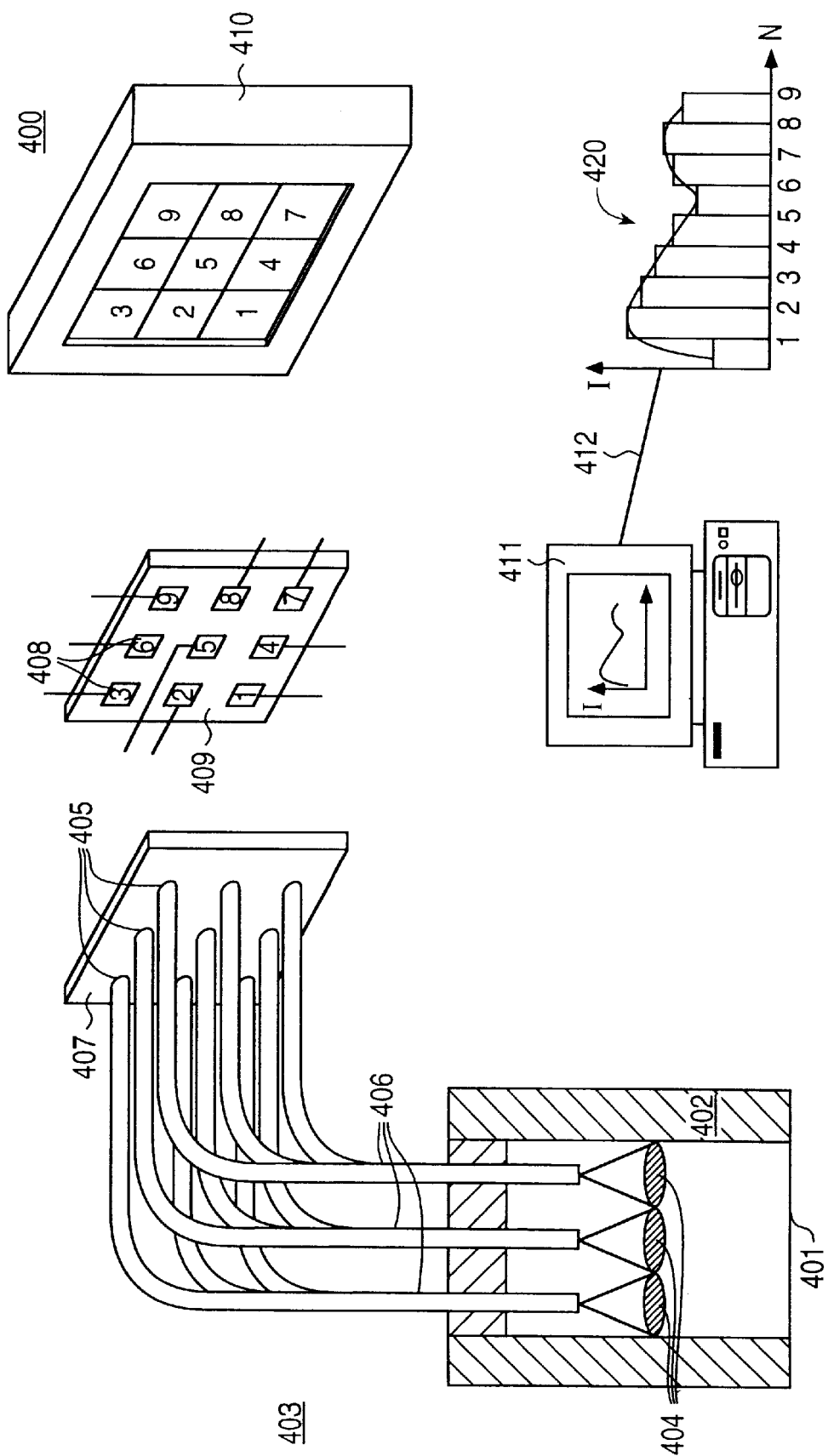
FIG. 6 depicts an embodiment of this invention using a system of filters of known spectrographic opacity positioned in front of a CCD.

FIG. 6 depicts a system 400 for collecting spectra of electromagnetic radiation across entrance 401 in head 402 of a directed fiber bundle probe 403. Fiber bundle probe 403 collects radiation entering into head 402 through entrance 401 by a plurality of lenses 404. This collected radiation is transmitted through fibers 406 onto tips 405 of fibers 406. Fibers 406 are arranged by fiber collector 407 in such a way that at each tip 405, a delivered portion of the total radiation is directed onto a pre-defined filter 408-1–408-9 of known opacity, each filter being the part of set of filters 409. Each of filters 408-1–408-9 of the set 409 is transparent for only radiation of particular (and known), narrow spectral range. The intensity of radiation passing through each filter is quantified by CCD 410. Each filter has a corresponding, pre-defined area on CCD 410, wherein filter number 1 corresponds to the area 1 on CCD 410, filter number 2 corresponds to the area 2 on CCD 410, etc. When the intensity detected at each area of CCD 410 is addressed to the spectral opacity range of each filter from the set, a spectrum 420 can be obtained using computer 411.

Example 5
Acquisition of Spectra from a Small Area

Figure 7:
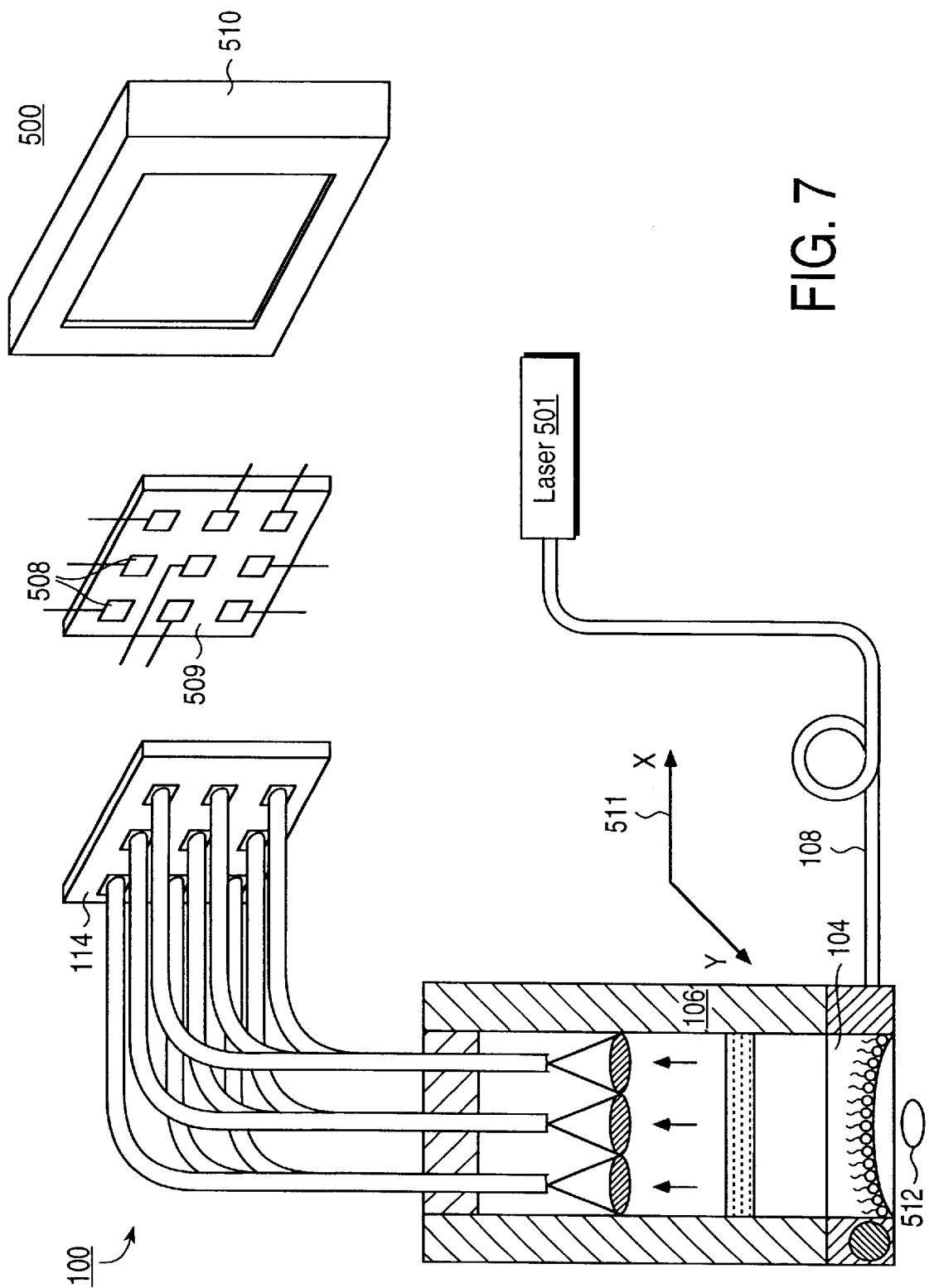
FIG. 7 depicts an embodiment of this invention for collecting spectra from a sample using filters of known spectrographic opacity.

FIG. 7 depicts a system 500 for collecting spectra of electromagnetic radiation emitted from a small area or space 104. Fiber bundle probe 100 for collecting light from a small area or space 104 described in FIG. 3 is used for collecting light emitted from a sample present in this space illuminated using laser 501. The excitation light from laser 501 is transmitted to the sample via fiber 108. Collected radiation from area 104 is directed onto a set 509 of filters 508 of pre-defined opacity and position via a waveguide array 114. The detection of intensities of radiation transmitted trough these filters 508 is performed by a CCD 510, each filter providing its corresponding intensity value. The position of head 106 of the directed fiber bundle probe 100 can be changed both in X and Y directions 511 to characterize larger areas. The sample and the head can be rotated relative to each other 512 for the avoidance of geometric dependence of the spectra.

Example 6
Microscopic Spectrographic Analysis

Figure 8:
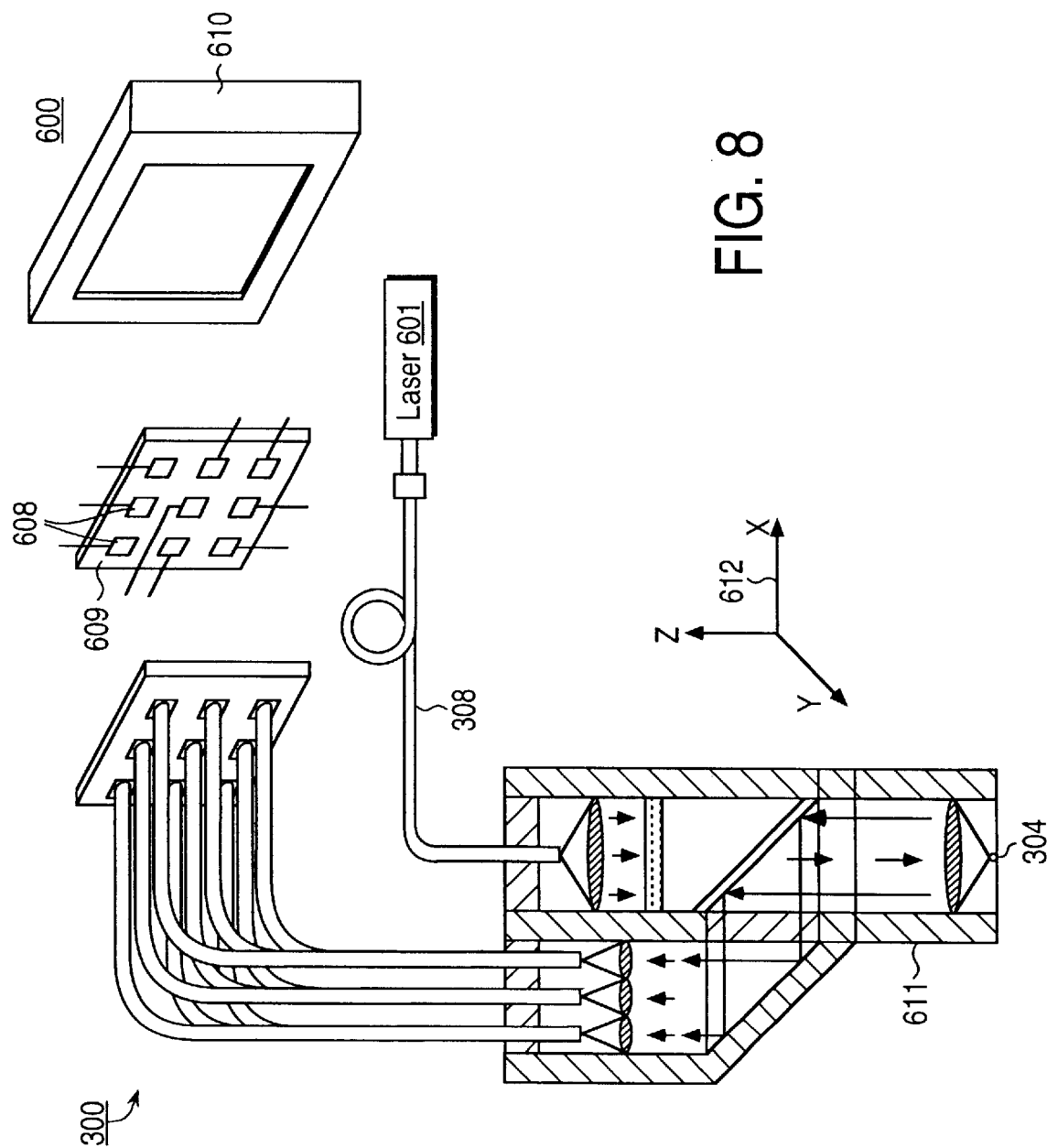
FIG. 8 depicts an embodiment of this invention for microscopic spectrographic characterization of samples.

FIG. 8 depicts a system 600 for collecting spectra of electromagnetic radiation emitted from a microscopic object 304. A directed fiber bundle probe 300 described in FIG. 3 collects light emitted from the sample upon its illumination with light emitted by a laser 601 and transmitted to the object by a fiber 308. Light emitted from the object 304 passes through a filter to cut off scattered excitation light, and is directed onto a set of filters 609 having pre-defined opacity and position. The detection of the intensities for the transmitted trough these filters 608 radiation is performed by CCD 610, each a filter 608 yielding its corresponding intensity value.

The position of head 611 of the directed fiber bundle probe 300 can be changed in X, Y and Z directions 612 to characterize the object in horizontal directions and to analyze its spectral properties, as dependent upon the depth of focus.

Example 7
Array Reader I

Figure 9A:
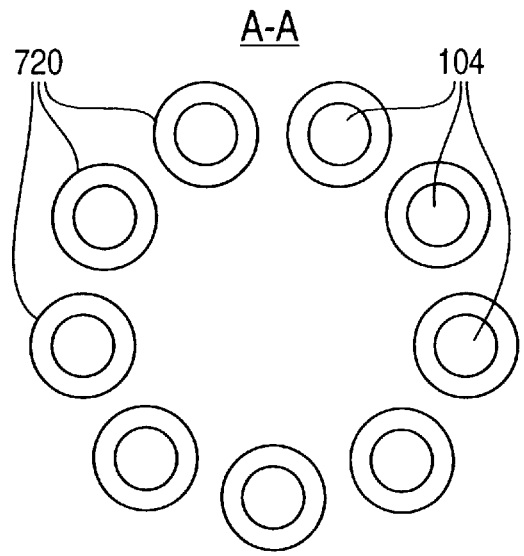
FIGS. 9a–9b depict an embodiment of this invention for simultaneous spectroscopic characterization of several areas.
Figure 9B:
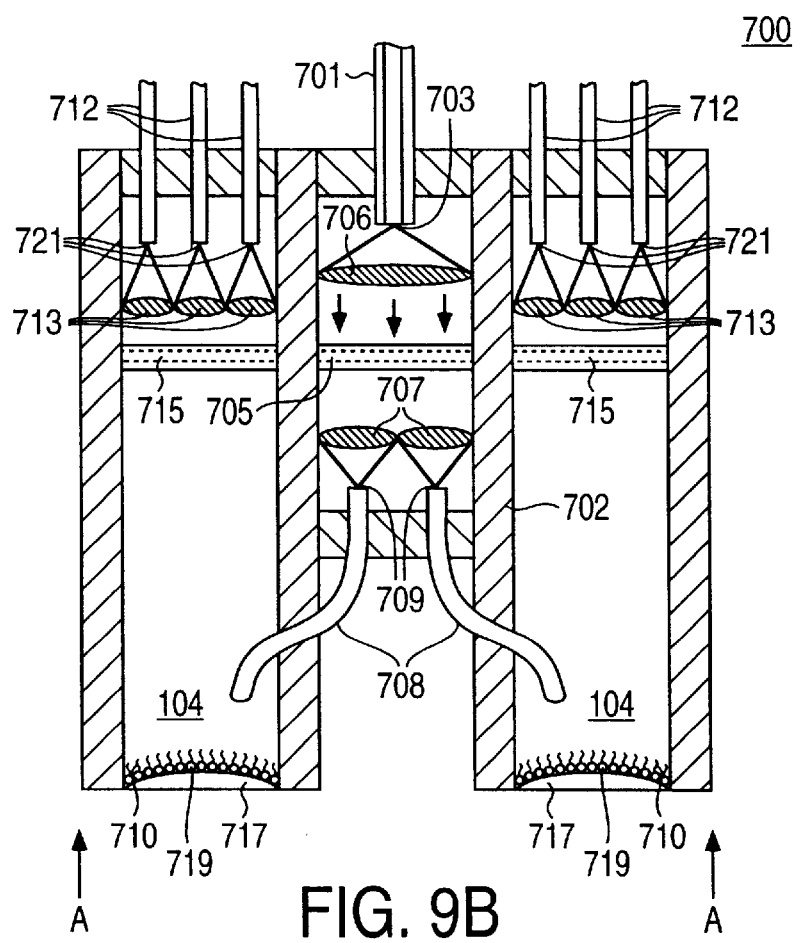

FIG. 9 depicts another embodiment of this invention, an array reader 700. FIG. 9a depicts a circular array of sample areas 720 with detection areas 104 therein. FIG. 9b depicts a side view of reader head 700. The array of sample areas 720 is illuminated via fibers 708 and directing the collected radiation by means of a bundle of fibers 712 arranged by a fiber collector (not shown). This probe 700 can be used for collecting radiation emitted from the spots of the array as the result of its illumination by an incident electromagnetic radiation or due to emission of electromagnetic radiation from these areas 104 due to any other phenomena. [0119] Illumination of the areas 104 is achieved by using light directed from a remote light source via fiber 701: Light coming into the excitation-light transmitting compartment 702 via fiber 201 is collected from the tip 703 of the fiber 201 by lens 706. Passage through an optical filter 705 (which can be a notch or a holographic filter transparent only for a desirable excitation wavelength) results in that light being collected by lenses 707 onto the tips 709 of the fibers 708. is essentially monochromatic. This is achieved by having each tip 709 of each of these fibers 708 in focus of a lens 707.

One use for the probe 700 is illustrated in FIG. 9b, which depicts the collection of Raman and/or fluorescence signals from an analyte 710 bound to a receptor 719, which is attached to SERS-active substrate 717. Upon excitation of the signal, light emitted from the areas 104 passes through a notch filter 715 to cut off the excitation light. Radiation passing through the filter is collected onto the entrances 721 of optical fibers 712 by lenses 713.

Example 8
Array Reader II

Figure 10:
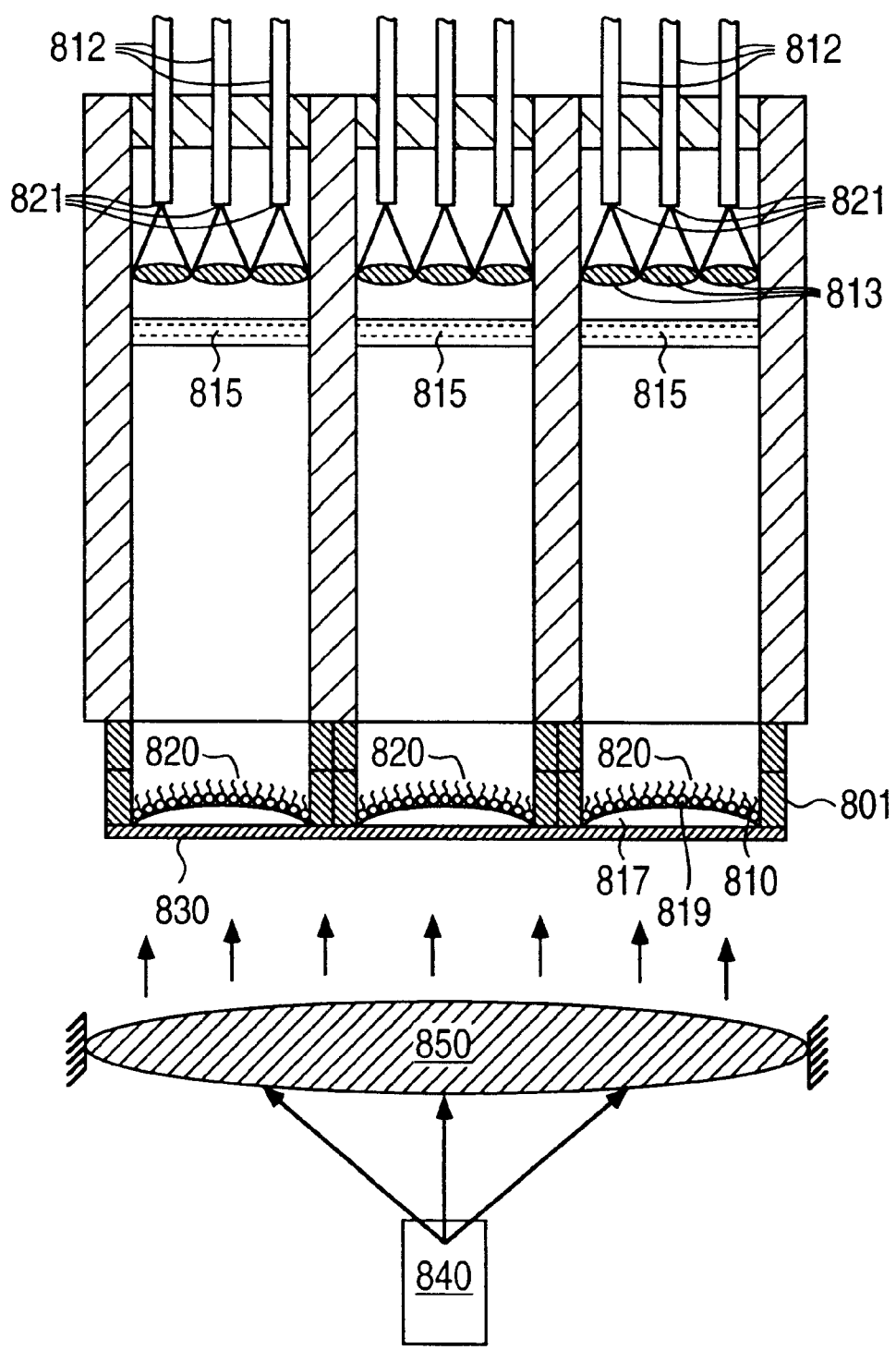
FIG. 10 depicts an embodiment of this invention for simultaneous spectroscopic characterization of several areas of a transparent sample.

In another embodiment of this invention, array reader 800, illumination of the areas 104 can be achieved to provide an MDR conditions by using an arrangement described in FIG. 10. FIG. 10 depicts a reader 800 for collecting light from small areas 104 of an array of spots 820. These spots 820 are deposited on a transparent substrate 830. Illumination is performed from the bottom of the array, using a source of monochromatic light 840, which is converted in a parallel beam by an optical system 850. Light coming onto the SERS-active substrate 817 with attached receptors 819 having analytes 810 bound thereto induces the emission of light from the spots 820. The emitted radiation passes a notch filter 815 to cut off the excitation light. Radiation passing through the filter is collected onto the entrances 821 of optical fibers 812 by lenses 813.

Example 9
Array Reader III

Figure 11:
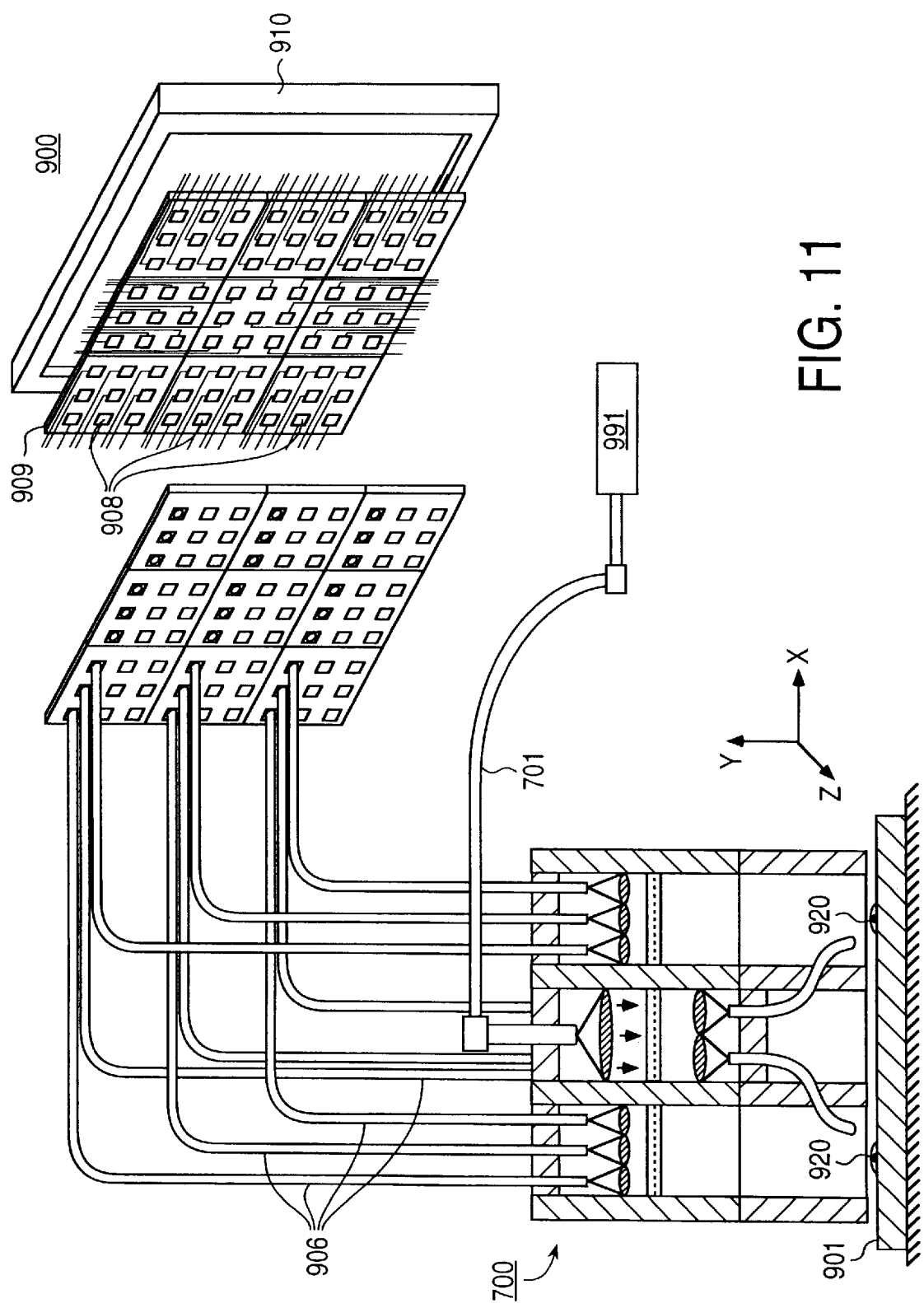
FIG. 11 depicts an alternative embodiment of this invention for simultaneous spectroscopic characterization of samples.

FIG. 11 depicts an array reader 900 in which a probe 700 is used to allow light from a laser 991 transmitted via a fiber 701 to illuminate an array 901 and to collect a signal from spots 920 of this array. Collected radiation from each spot 920 of the array 901 is devoid of the contribution of excitation light, and collected radiation is directed onto a fiber collector 907 via optical fiber bundle 906. Each fiber of this bundle has its defined position 905 on the fiber collector 907. In addition, the fibers of the bundle 906 are arranged by the fiber collector 907 in such a way that each fiber is directed onto a predefined filter 908 of known opacity, each being the part of set of filters 909. Each filter 908 of the set 909 is transparent for only radiation of particular (and known), narrow, spectral range. The intensities of delivered by each fiber and passed through each filter radiation are determined. This is achieved by having the position for each filter and each fiber addressed on a CCD 910. As the result of such arrangement, the spectrum of each spot can be identified.

Example 10
Double-beam Spectrophotometer

Figure 12:
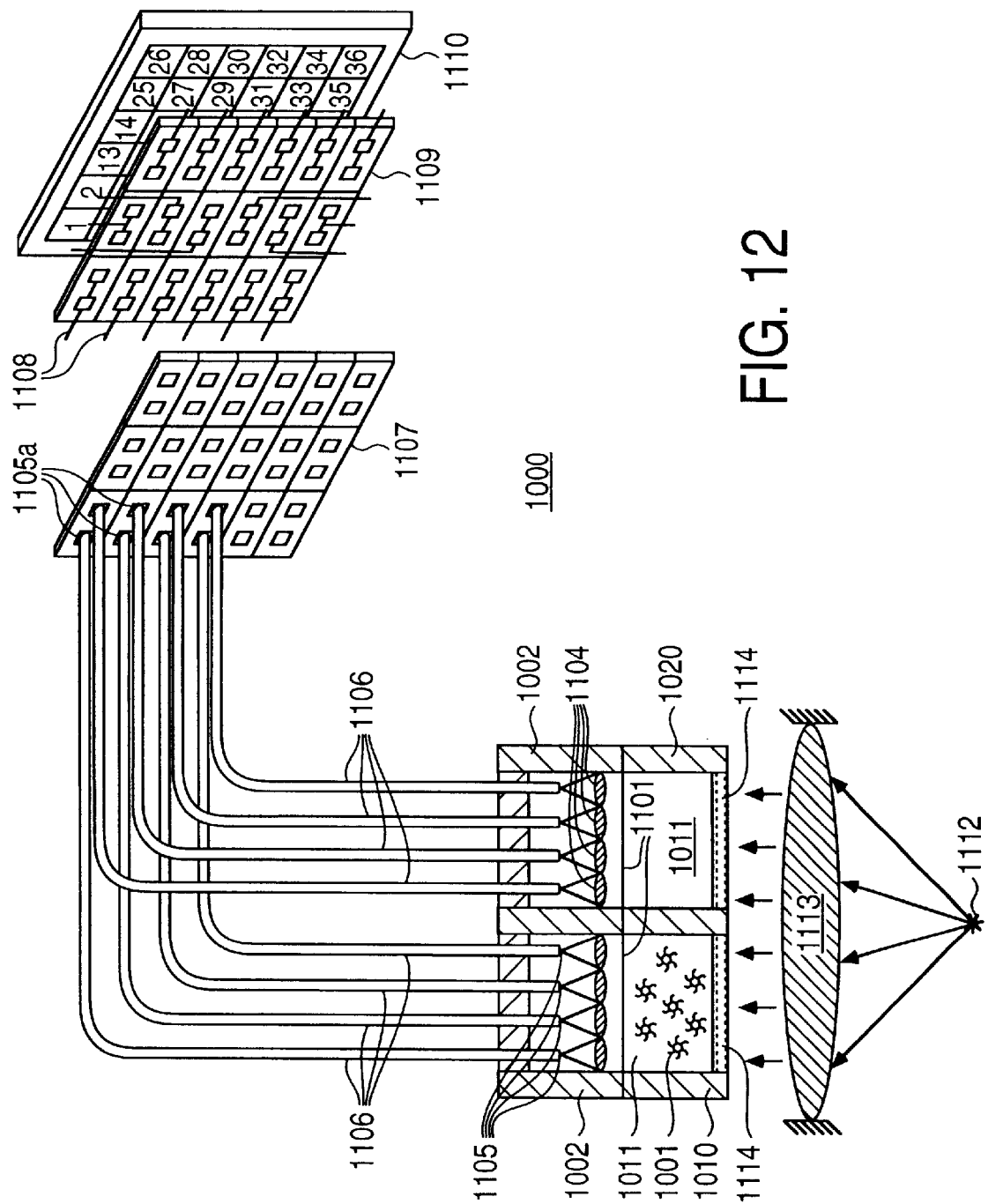
FIG. 12 depicts an embodiment of this invention having a double beam spectrophotometer.

FIG. 12 depicts a double beam spectrophotometer 1000 of this invention, in which light passes through a sample cuvette 1010 with an analyte 1001 in solvent 1011 and light passes through a control cuvette 1020 with the solvent 1011. Spectrographic information is simultaneously acquired using a two heads 1002 of a directed fiber bundle probe. Light source 1112 provides white light. This light is collimated by an optical system 1113 and passes trough transparent bottoms 1114 of cuvettes 1010 and 1020. Each head of this fiber probe collects by a system of lenses 1104 essentially all radiation entering into the heads through the entrances 1101. This collected radiation is transmitted through the fibers 1106 onto the tips 1105 of the fibers 1106. These fibers 1106 are arranged by a fiber collector 1107 in such a way that at each tip 1105a, a delivered portion of total radiation is directed onto a pre-defined filter 1108-1 to 1108-36 of known opacity, each filter being the part of set of filters 1109. Each filter 1108-1 to 1108-36 of this set 1109 is transparent for only radiation of particular (and known), narrow, spectral range. The intensity of radiation passing through each filter is determined by CCD 1110. In addition, each fiber has its correspondent pre-defined area on the CCD so as each filter has two areas for fibers coming from the sample cuvette 1010 and from control cuvette 1020, and these two areas have correspondent areas on CCD. When the intensity detected at each of these areas of CCD is addressed to the spectral opacity range of each filter from the set, a spectrum can be obtained using a computer for both the analyte and for the solvent. Comparison between the two spectra yields the absorption spectrum of the analyte.

Example 11
Alternative Waveguide Configurations

Figure 13A:
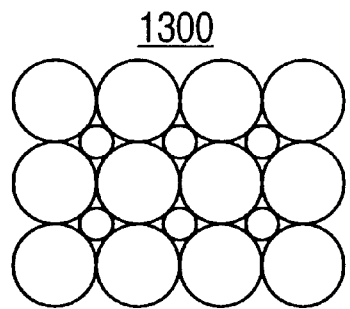
FIGS. 13a–13d depict embodiment of this invention in which waveguides of different sizes and/or shapes are arranged.
Figure 13B:
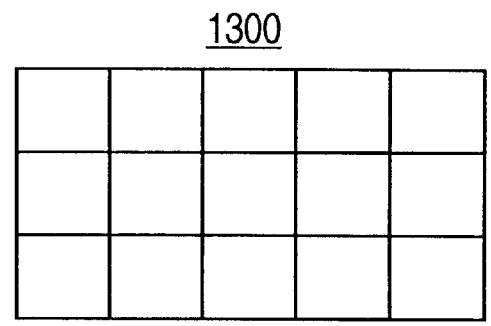
Figure 13C:
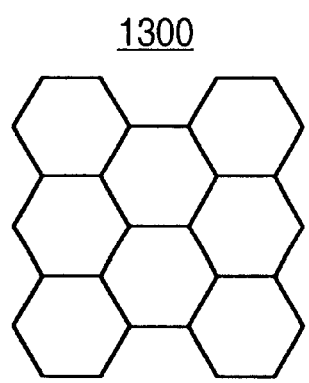
Figure 13D:
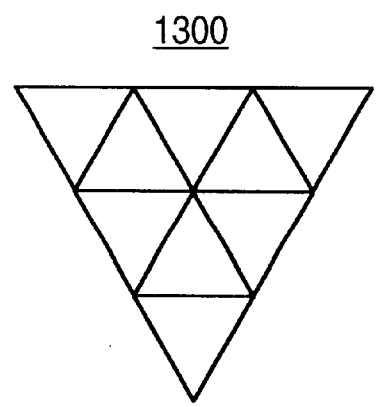
Figure 14A:
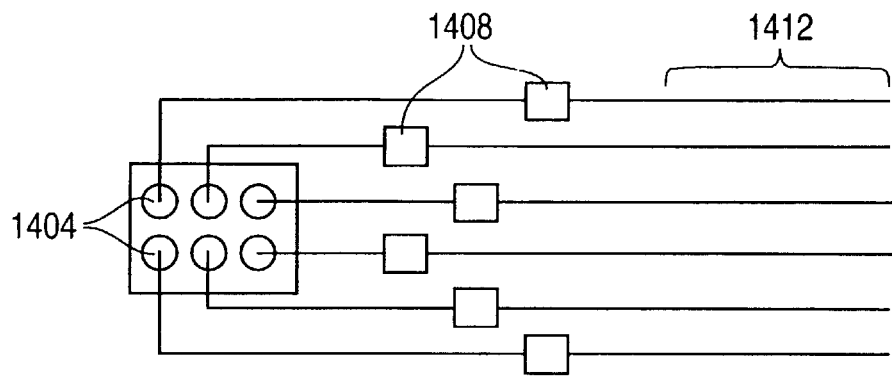
FIGS. 14a–14b depicts an embodiment of this invention in which a plurality of waveguides carries electromagnetic radiation to a plurality of detectors arranged in a three-dimensional array.
Figure 14B:
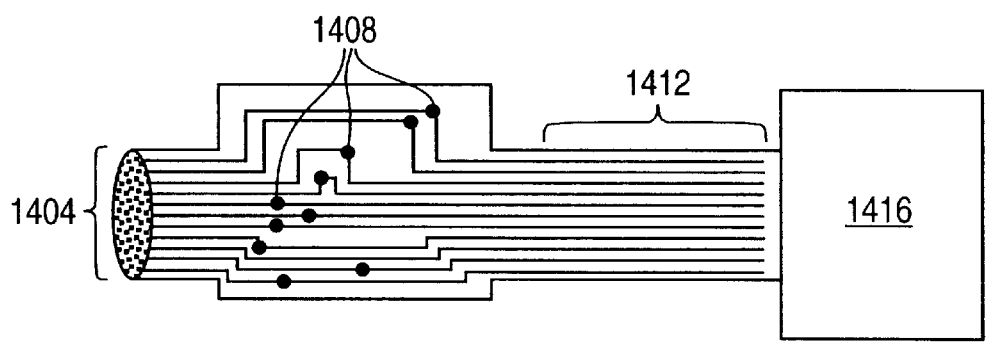
Figure 15:
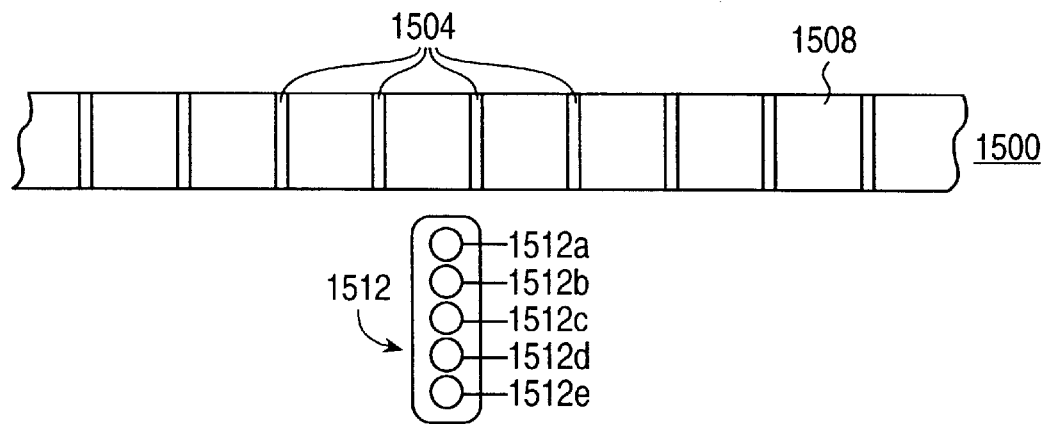
FIG. 15 depicts an embodiment of this invention in which a series of samples on a substrate are detected using a filter-based spectrographic probe.

FIGS. 13a–13d depict alternative configurations of waveguides in a probe tip 1300 of this invention. In FIG. 13a, a first size of waveguide 1304 is arranged in a hexagonal array with spaces between the waveguides. A second size of waveguide 1308 is sufficiently small to be placed within the interstices between waveguides 1304, thereby increasing the total surface area of the probe 1300. In FIG. 13b, rectangular waveguides 1312 are arranged in a pattern that can maximize the acquisition of radiation emitted by a sample. In FIG. 13c, an alternative plurality of hexagonal waveguides 1316 is arranged in an array that maximizes the acquisition of radiation emitted from a sample. FIG. 13d depicts an alternative configuration of triangular waveguides 1320 that can maximize acquisition of radiation emitted by a sample Example 12
Waveguide Detector Bundle FIGS. 14a–14b depict alternative embodiments 1400 of this invention in which a plurality of waveguides 1404 transmit radiation to a plurality of detectors 1408 such as photodiodes, that are arranged in series, with one photodetector associated with each waveguide. In these embodiments, as depicted in FIG. 14b, a relatively large number of waveguides and detectors can be bundled together in a three-dimensional array 1408, thereby minimizing the volume of space necessary to capture and transmit radiation and covert it into electrical information. Electrical cable 1412 transmits electrical signals produced by detectors 1408 to a processor 1416.

Photodiodes of sizes ranging from about 0.5 $\mu$m to about 1 mm are commercially available, but smaller sized photodiodes can be made sufficiently small to be compatible with waveguides of sizes in the range of about 1 nm or greater. It is not necessary that the photodiodes have diameters comparable to those of waveguides. As depicted in FIG. 14b, photodetectors having diameters larger than the waveguide can be packaged in a three-dimensional array, wherein different planes of photodetectors have waveguides of different lengths. Thus, a large number of individual photodetector/waveguide pairs can be packaged in a relatively small space, making the reader portable.

Example 13
Strip Detector

FIG. 1 depicts another alternative embodiment of this invention 1500 in which a series of samples 1504 are arrayed along a strip of a substrate 1508. Additional portions of strip 1508 are depicted in a source reel (not shown) and a take-up reel (not shown), which contain additional samples therein. A reader probe 1512 is depicted near each sample 1504. Reader probe 1512 is placed over each sample 1504 and spectrographic information obtained at a plurality of wavelengths a–e by a plurality of individual waveguides with filters 1512a–1512e selective for wavelengths a–e in each sample 1504. Strip of substrate 1508 can be moved relative to reader probe 1512 so that each of samples 1504 can be read by reader probe 1512. In this way, a plurality of samples can be collected, stored and transported to an analysis system for spectrographic analysis of a large number of samples.

The samples can be either substantially circular, oblong, or linearly arranged wherein the sample can have a longitudinal axis and a minor axis, and wherein the longitudinal axis of the sample is arranged approximately perpendicular to the axis of the strip. In this way, a plurality of samples having a substantial number of sites for spectrographic measurements can be placed on the strip and to be read by the strip reader. However, it is apparent that the longitudinal axis of a sample need not be substantially perpendicular to the longitudinal axis of the substrate. A variety of orientations of samples on such strips can be used with satisfactory results.

Example 14
Reader System I

Figure 16:
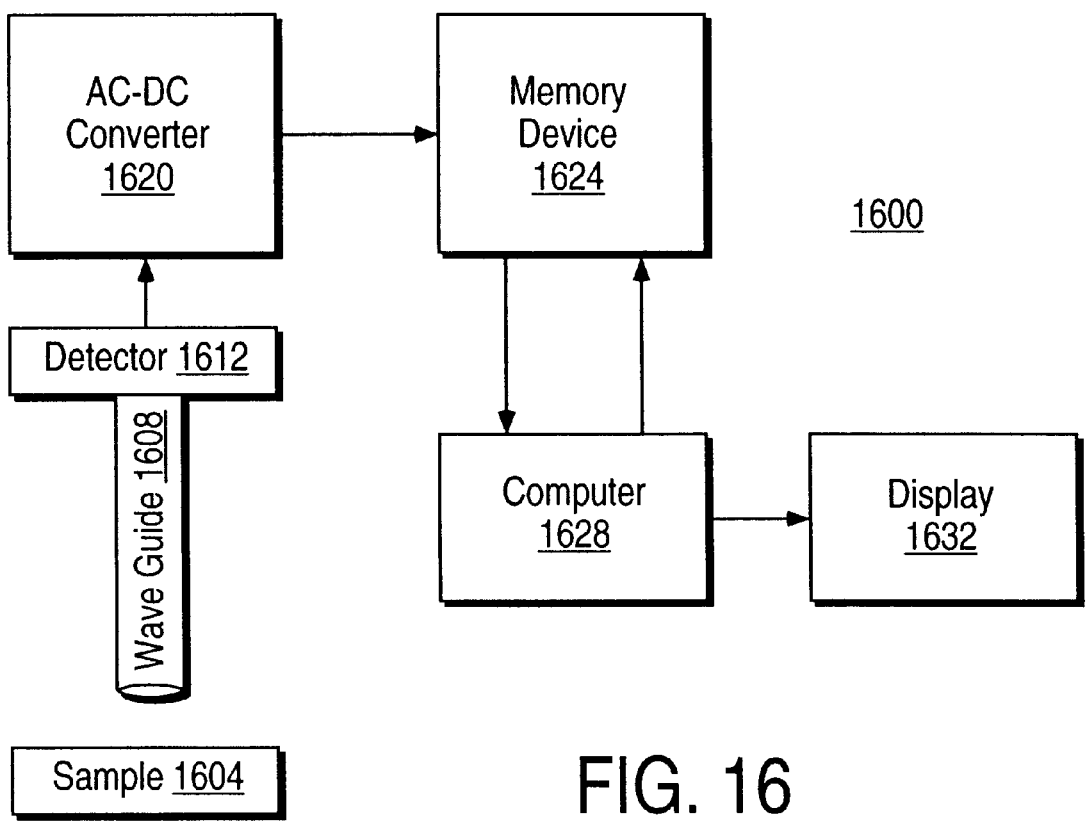
FIG. 16 depicts a schematic representation of an embodiment of a spectrographic reader and system of this invention.

FIG. 16 depicts a schematic representation of a system 1600 for filter/based spectrographic analysis. Sample 1604 is shown relative to waveguide 1608 and detector 1612 having a filter associated therewith (not shown). Electrical signals from detector 1612 are transmitted to alternating current–direct current (AC-DC) converter 1620, where the signal is digitized. Digitized information is transmitted to memory device 1624. Information in memory device 1624 is transmitted to and/or from computer 1628 for analysis, and the analyzed information is then transmitted to plotter 1632 for display.

Example 15

Reader System II

Figure 17:
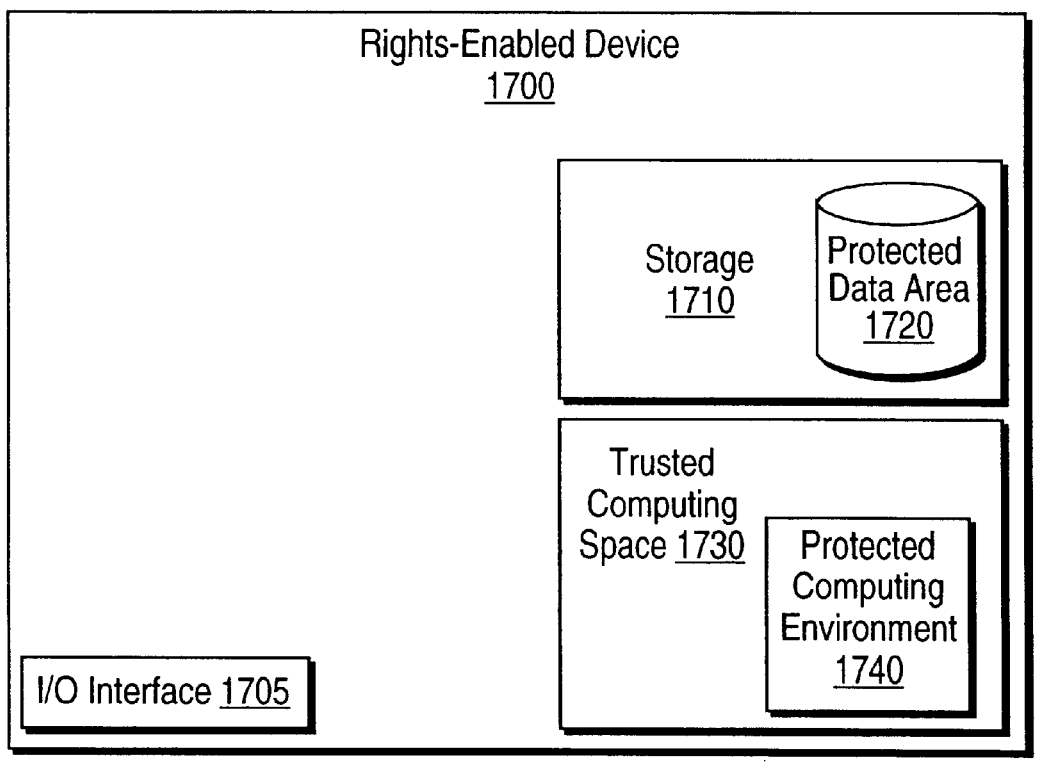
FIG. 17 depicts a schematic representation of a rights-enabled device with trusted computing space used with the reader and system of this invention.
Figure 18:
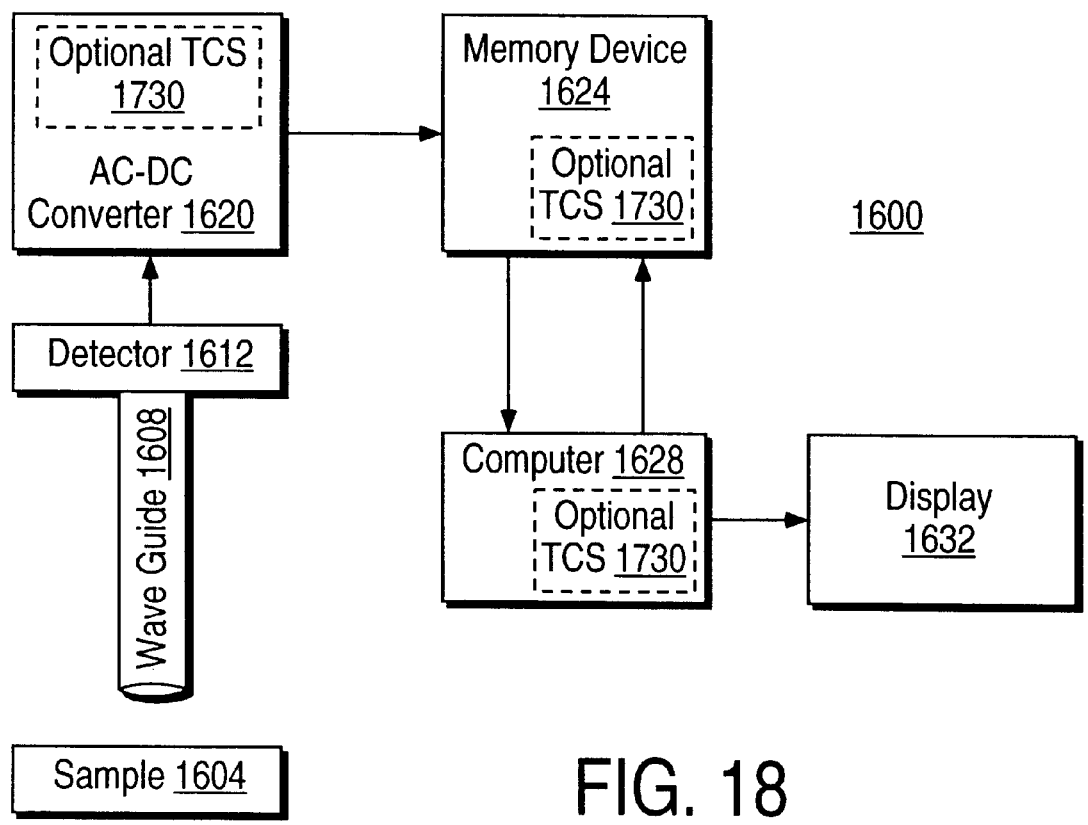
FIG. 18 depicts a schematic representation of a spectrographic reader and system with optional digital rights management components.

FIGS. 17 and 18 depict embodiments of this invention incorporating rights enabling devices. FIG. 17 depicts a rights-enabled device 1700 having an input output interface 1705, a storage device 1710 with a protected data area 1720, a trusted computing space 1730 having a protected computing environment 1740 therein.

FIG. 18 depicts an embodiment of this invention incorporating rights-enabled devices described in FIG. 17. Sample 1604 is shown in relation to waveguide 1608 and detector 1612. Electrical signals from detector 1612 are transmitted to alternating current-direct current (AC-DC) converter 1620 having a trusted computer space (TCS) 1730. Digitized information from AC-DC converter 1620 is transmitted to memory device 1624 having trusted computer space 1730. Information from memory device 1624 is exchanged with computer 1628 having trusted computer space 1730. Information is transmitted from computer 1628 to display device 1632.

Example 16

System for Reading Addressable Arrays

Figure 19A:
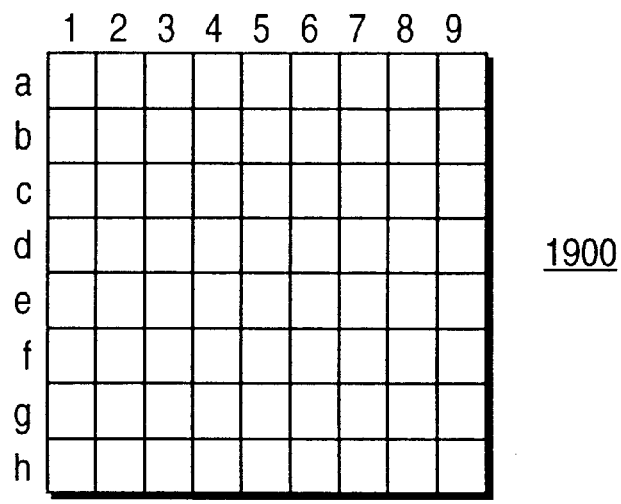
FIGS. 19a and 19b depict a system of this invention for analyzing spectrographic information from a plurality of samples in an addressable array.
Figure 19B:
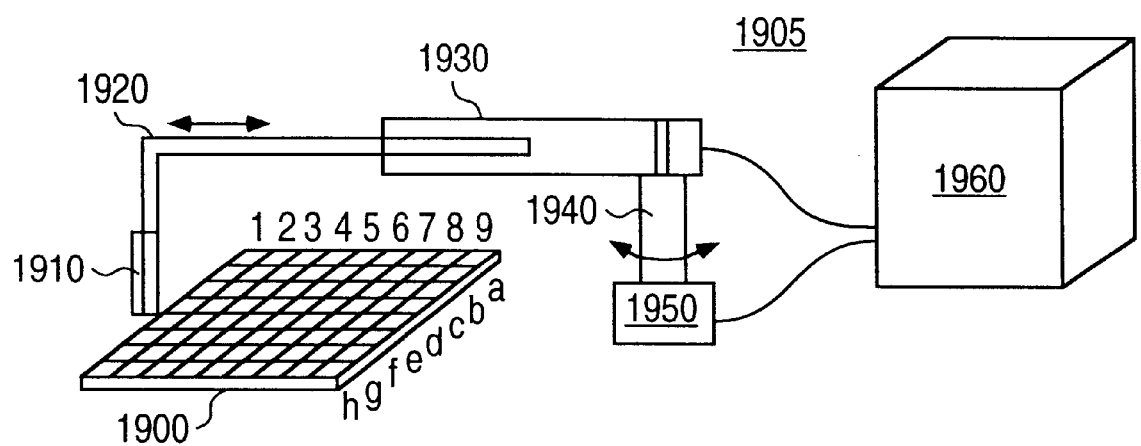

FIGS. 19a and 19b depict an embodiment of this invention for reading addressable arrays of samples on a substrate. FIG. 19a depicts an addressable two-dimensional array of samples on a substrate 1900 having 9 columns (1–9) and 8 rows (a–h). The addresses of each sample location are represented as a pair of coordinates in the X (columns) and Y (rows) directions. The address at column 1, row a (1a) represents the positional address of the upper left most sample area and the address at column 9, row h (9h) represents the lower right most sample area. Samples are provided on one or more addressable locations and the substrate.

FIG. 19b depicts a system 1905 for spectrographic analysis of samples incorporating the addressable array of FIG. 19a. Substrate 1900 is depicted in relation to a probe tip 1910 comprising filter/waveguide/detector elements therein. Probe tip 1910 is held by arm 1920, which is held by sleeve 1930. Arm 1920 is slidably moveable in sleeve 1930 by an actuator (not shown) that is controlled by computer 1960. Movement of arm 1920 toward the left of the figure place the probe toward lower column numbers. Sleeve 1930 has a vertical element 1940 that is fixed near the right end of sleeve 1930. Element 1940 is shown rotatable about an axis by motor 1950. Rotation of element 1940 in the clockwise direction as viewed from above moves the probe 1910 toward lower rows (e.g. row a), and movement in the counterclockwise direction moves probe 1910 toward higher rows (e.g., row f). The positions of element 1940 and arm 1920 are controlled by computer 1960, so that a desired address can be selected from the computer. Upon movement of probe 1910 to an addressable location, spectrographic information is recorded and stored in computer 1960. Subsequently, probe 1910 is moved to another address and additional spectrographic information is collected and stored in computer 1960.

The examples depicted above are intended only to illustrate the general concepts and some embodiments of this invention, and are not intended to be limiting. Persons of skill in the art can readily appreciate that the concepts of this invention can be used to create a wide variety of different devices and methods for spectrographic analysis. All of those variations are included within the scope of this invention.

We claim:

1. A device for obtaining spatially resolved spectrographic information, comprising:
   (a) a plurality of spatially addressable fibers;
   (b) one or more filters, each filter having a defined wavelength range of electromagnetic radiation that can pass therethrough;
   (c) each of said fibers associated with one of said filters; and
   (d) a plurality of addressable detectors, each detector associated with one of said fibers.

2. The device of claim 1, further comprising a memory device for storing said spectrographic information.

3. The device of claim 1, further comprising a computer.

4. The device of claim 1, further comprising a display device.

5. The device of claim 1, further comprising an AC-DC converter.

6. The device of claim 2, wherein said memory device has at least one protected data area.

7. The device of claim 3, wherein said computer has at least one trusted computing space.

8. The device of claim 1, further comprising a plurality of waveguides, wherein each of said filters is associated with at least one of said waveguides.

9. The device of claim 8, wherein said plurality of waveguides is arranged in a fiber bundle.

10. The device of claim 8, wherein said waveguides have circular cross-section.

11. The device of claim 8, wherein said waveguides have rectangular cross-section.

12. The device of claim 8, wherein said waveguides have triangular cross-section.

13. The device of claim 10, wherein said waveguides are arranged in a square array.

14. The device of claim 10, wherein said waveguides are arranged in a hexagonal array.

15. The device of claim 10, wherein said waveguides have different diameters.

16. The device of claim 9, wherein said fiber bundle is adapted to be positioned relative to a predetermined location on a substrate.

17. The device of claim 1, further comprising at least one waveguide.

18. The device of claim 17, wherein said at least one waveguide is associated with a focusing device.

19. The device of claim 18, wherein said focusing device is a lens.

20. The device of claim 18, wherein said focusing device focuses electromagnetic radiation emitted from a sample onto a tip of said waveguide.

21. An array reader comprising:
   (a) a source of electromagnetic radiation;
   (b) a probes associated with said source, said probe comprising a plurality of spatially addressable fibers;
   (c) one or more filters, each filter having a defined wavelength range of electromagnetic radiation that can pass therethroug;
   (d) each of said fibers associated with one of said filters;
   (e) a plurality of addressable detectors, each detector associated with one of said fibers;
   (f) a memory device capable of storing spectrographic information obtained from said plurality of detectors;
   (g) a computer capable of processing information obtained from said memory device; and
   (h) an output device.

22. The array reader of claim 21, further comprising an AC-DC converter.

23. The array reader of claim 21, wherein said memory device has at least one protected data area.

24. The array reader of claim 21, wherein said computer has at least one trusted computing space.

25. The array reader or claim 21, wherein said memory device has at least one protected data area and wherein said computer has at least one trusted computing space.

26. The array reader of claim 21, wherein sad source of electromagnetic radiation is a laser.

27. The array reader of claim 21, wherein said probe is at least in part positionable relative to a preselected location on a substrate.

28. The array reader of claim 21, adapted to detect Raman radiation emitted by a sample.

29. The array reader of claim 21, adapted to detect fluorescent radiation emitted by a sample.

30. A system for spectrographic analysis of a sample, comprising:
  (a) a source of electromagnetic radiation;
  (b) a probes associated with said source, said probe comprising a plurality of spatially addressable fibers;
  (c) one or more filters, each filter having a defined wavelength range of electromagnetic radiation that can pass therethrough;
  (d) at least one fiber associated with a filter;
  (e) a plurality of addressable detectors, each detector associated with one of said fibes;
  (f) a memory device capable of storing spectrographic information obtained from said plurality of detectors;
  (g) a computer capable of processing information obtained from said memory device; and
  (h) an output device for displaying information processed by said computer.

31. The system of claim 30, wherein said sample comprises a substrate.

32. The system of claim 31, wherein said substrate has an analyte receptor thereon.

33. The system of claim 32, wherein said analyte receptor has an analyte bound thereto.

34. The system of claim 30, wherein said sample is on a substrate having a plurality of samples thereon.

35. The system of claim 34, wherein at least one of said plurality of said samples is different from other of said plurality of samples.

36. The system of claim 34, wherein said plurality of samples is arranged in an addressable array.

37. The system of claim 36, wherein said addressable array is a one-dimensional array.

38. The system of claim 36 wherein said addressable array is a two-dimensional array.

39. The system of claim 34, wherein said substrate is substantially planar.

40. The system of claim 34, wherein said substrate is flexible.

41. The system of claim 34, where each of said samples is associated with an address on said array.

42. The system of claim 30, wherein said sample is substantially circular.

43. The system of claim 30, wherein said sample is oblong.

44. The system of claim 30, wherein said sample is substantially rectangular.

45. A method for obtaining spectrographic information from a sample comprising:
  (a) illuminating said sample with incident electromagnetic radiation; and
  (b) obtaining electromagnetic radiation emitted by said sample using a probe, said probe comprising:
    (i) a plurality of spatially addressable fibers;
    (ii) one or more filters, each filter having a defined wavelength range of electromagnetic radiation that can pass therethrough;
    (iii) each of said fibers associated with one of said filters; and
    (iv) a plurality of addressable detectors, each detector associated with one of said fibers.

46. The method of claim 45, further comprising storing said spectrographic information in a memory device.

47. The method of claim 45, further comprising analyzing said spectrographic information using a computer.

48. The method of claim 47, wherein said memory device has at least one protected data area and said step of storing comprises storing said information in said at least one protected data area.

49. The method of claim 47, wherein said computer has at least one trusted computing space and said step of analyzing comprises analyzing said spectrographic information in said trusted computing space.

50. The method of claim 45, wherein said substrate has a Raman enhancing structure thereon.

51. The method of claim 50, wherein said sample is near said Raman enhancing structure.

52. The method of claim 45, wherein said Raman enhancing structure has an analyte receptor bound thereto.

53. The method of claim 52, wherein said sample is an analyte bound to said analyte receptor.

54. A device for obtaining spatially resolved spectrographic information, comprising:
  (a) a plurality of filters, each having a defined wavelength range of electromagnetic radiation that can pass therethrough;
  (b) a plurality of addressable detectors, each associated with one of said filters; and
  (c) a plurality of addressable waveguides, each of said of waveguides associated with one of said detectors.

55. The array reader of claim 21 adapted to detect luminescent radiation.

56. The array reader of claim 21 adapted to detect chemiluminescent radiation.

57. The array reader of claim 21 adapted to detect bioluminescent radiation.

58. The device of claim 1, wherein at least one of said plurality of detectors comprises a charge coupled device (CCD).

59. The system of claim 31, wherein said substrate has particle structures thereon that enhance electromagnetic radiation.

60. The system of claim 59, wherein at least one of said particle structures has an analyte receptor thereon.

61. The system of claim 60, wherein said particle structure has a passivation layer thereon.

* * * * *